(12) United States Patent
Drew et al.

(10) Patent No.: US 10,946,162 B2
(45) Date of Patent: Mar. 16, 2021

(54) SYSTEM AND METHOD FOR ON-DEMAND NEAR-PATIENT HUMIDIFICATION

(71) Applicant: TELEFLEX MEDICAL INCORPORATED, Morrisville, NC (US)

(72) Inventors: Douglas Drew, Raleigh, NC (US); Daniel Patrick Dwyer, Cary, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 258 days.

(21) Appl. No.: 15/794,708

(22) Filed: Oct. 26, 2017

(65) Prior Publication Data

US 2018/0110955 A1    Apr. 26, 2018

Related U.S. Application Data

(60) Provisional application No. 62/413,154, filed on Oct. 26, 2016.

(51) Int. Cl.
*A61M 16/10* (2006.01)
*A61M 16/08* (2006.01)
(Continued)

(52) U.S. Cl.
CPC ...... *A61M 16/1075* (2013.01); *A61M 16/024* (2017.08); *A61M 16/0808* (2013.01);
(Continued)

(58) Field of Classification Search
CPC .......... A61M 16/1045; A61M 16/1075; A61M 16/161; A61M 16/162; A61M 2205/3368;
(Continued)

(56) References Cited

U.S. PATENT DOCUMENTS

| 3,865,106 A | 2/1975 | Palush |
| 4,013,742 A | 3/1977 | Lang |

(Continued)

FOREIGN PATENT DOCUMENTS

| AU | 2008202098 A1 | 2/2009 |
| CN | 204798549 U | 11/2015 |

(Continued)

OTHER PUBLICATIONS

Partial supplementary European search report for EP Application No. 17864363.1, dated May 20, 2020.

(Continued)

*Primary Examiner* — Samchuan C Yao
*Assistant Examiner* — Nathan M Le
(74) *Attorney, Agent, or Firm* — BakerHostetler

(57) ABSTRACT

A near-patient humidification system provides vapor to a respiratory breathing circuit. The system includes an expiratory gas conduit and an inspiratory gas conduit. A patient coupling member is provided for coupling the expiratory and inspiratory gas conduits to a patient interface. A vapor injection unit is located at least partially within the housing of the patient coupling member. The vapor injection unit heats a supply of fluid into vapor and injects the vapor into the inspiratory gas passage of the patient coupling member at a vapor injection location for providing moisture to the inspiratory gas flow. A method of simultaneously and independently controlling the temperature and humidity of inspiratory gas in a respiratory breathing circuit is performed by injecting vapor having a temperature determined as a function of measured temperatures and measured humidities of the breathing gas at different locations along the breathing circuit.

25 Claims, 22 Drawing Sheets

(51) Int. Cl.
*A61M 16/16* (2006.01)
*H05B 3/44* (2006.01)
*A61M 16/00* (2006.01)

(52) U.S. Cl.
CPC .... *A61M 16/0816* (2013.01); *A61M 16/0875* (2013.01); *A61M 16/109* (2014.02); *A61M 16/1045* (2013.01); *A61M 16/16* (2013.01); *A61M 16/161* (2014.02); *H05B 3/44* (2013.01); *A61M 16/0833* (2014.02); *A61M 16/162* (2013.01); *A61M 2016/003* (2013.01); *A61M 2016/0027* (2013.01); *A61M 2205/3331* (2013.01); *A61M 2205/3368* (2013.01); *A61M 2205/7536* (2013.01); *H05B 2203/014* (2013.01); *H05B 2203/021* (2013.01); *H05B 2203/022* (2013.01)

(58) Field of Classification Search
CPC ............ A61M 16/024; A61M 16/0808; A61M 16/0816; A61M 16/0833; A61M 16/0875; A61M 16/109; A61M 16/16; A61M 2016/0027; A61M 2016/003; A61M 2205/3331; A61M 2205/7536; A61M 16/08; A61M 16/0883; A61M 39/00; A61M 39/08; A61M 16/14; H05B 2203/014; H05B 2203/021; H05B 2203/022; H05B 3/44
See application file for complete search history.

(56) References Cited

U.S. PATENT DOCUMENTS

| | | | |
|---|---|---|---|
| 4,028,445 A | 6/1977 | Hickmann et al. | |
| 4,430,994 A | 2/1984 | Clawson et al. | |
| 4,621,632 A | 11/1986 | Bartels et al. | |
| 4,910,384 A | 3/1990 | Silver | |
| 4,967,744 A | 11/1990 | Chua | |
| 5,222,185 A | 6/1993 | McCord, Jr. | |
| 5,286,942 A | 2/1994 | McFadden et al. | |
| 5,613,505 A | 3/1997 | Campbell et al. | |
| 6,095,505 A | 8/2000 | Miller | |
| 6,394,084 B1* | 5/2002 | Nitta | A61M 16/16 128/201.13 |
| 6,681,998 B2 | 1/2004 | Sharpe et al. | |
| 6,787,742 B2 | 9/2004 | Kansa et al. | |
| 6,802,314 B2 | 10/2004 | McPhee | |
| 6,827,046 B2* | 12/2004 | Welle | B01B 1/005 122/367.1 |
| 6,918,389 B2 | 7/2005 | Seakins et al. | |
| 6,921,042 B1* | 7/2005 | Goodzeit | H01F 7/202 242/430 |
| 6,923,179 B2 | 8/2005 | Gupta et al. | |
| 6,976,489 B2* | 12/2005 | Mantell | A61M 13/003 128/204.17 |
| 7,031,160 B2 | 4/2006 | Tillotson | |
| 7,938,113 B2 | 5/2011 | Weinstein et al. | |
| 8,052,127 B2 | 11/2011 | Nichols et al. | |
| 8,282,084 B2 | 10/2012 | Nichols et al. | |
| 8,327,845 B2 | 12/2012 | Weinstein et al. | |
| 8,662,479 B2 | 3/2014 | Nichols et al. | |
| 9,314,582 B2 | 4/2016 | Korneff et al. | |
| 2002/0078956 A1* | 6/2002 | Sharpe | A61M 11/042 128/203.26 |
| 2003/0111077 A1 | 6/2003 | Hooser et al. | |
| 2004/0055597 A1 | 3/2004 | Virr et al. | |
| 2004/0102731 A1 | 5/2004 | Blackhurst et al. | |
| 2004/0151598 A1 | 8/2004 | Young et al. | |
| 2005/0095168 A1* | 5/2005 | Centanni | H05B 6/108 422/3 |
| 2006/0012057 A1* | 1/2006 | Anthony | A61M 16/1075 261/154 |
| 2006/0047368 A1 | 3/2006 | Maharajh et al. | |
| 2006/0184096 A1* | 8/2006 | Ott | A61M 13/003 604/26 |
| 2006/0220267 A1* | 10/2006 | Kabasawa | B01B 1/005 261/142 |
| 2007/0277825 A1 | 12/2007 | Bordewick et al. | |
| 2008/0066751 A1 | 3/2008 | Polacsek | |
| 2008/0236577 A1 | 10/2008 | Power et al. | |
| 2009/0133697 A1 | 5/2009 | Kwok et al. | |
| 2009/0267242 A1 | 10/2009 | Nichols et al. | |
| 2009/0312661 A1* | 12/2009 | Kullik | A61B 5/0876 600/538 |
| 2010/0000980 A1* | 1/2010 | Popescu | A47J 36/2466 219/201 |
| 2011/0108031 A1* | 5/2011 | Korneff | A61M 16/0875 128/203.27 |
| 2012/0017905 A1* | 1/2012 | Sata | A61M 16/1075 128/203.26 |
| 2013/0081617 A1 | 4/2013 | Cavendish | |
| 2013/0112201 A1 | 5/2013 | Graham et al. | |
| 2013/0263845 A1* | 10/2013 | Arcilla | A61M 11/006 128/200.14 |
| 2013/0284165 A1 | 10/2013 | Krimsky | |
| 2013/0284169 A1* | 10/2013 | Foote | A61M 16/0833 128/203.14 |
| 2014/0305431 A1* | 10/2014 | Holley | A61M 16/208 128/201.13 |
| 2014/0373835 A1* | 12/2014 | Ahmad | A61M 16/0875 128/203.12 |
| 2015/0083126 A1* | 3/2015 | Rogers | A61M 16/026 128/203.14 |
| 2015/0114504 A1 | 4/2015 | Cecka et al. | |
| 2015/0115483 A1* | 4/2015 | Miller | A61M 16/16 261/128 |
| 2015/0320116 A1* | 11/2015 | Bleloch | H05B 6/108 219/628 |
| 2015/0328431 A1* | 11/2015 | Arcilla | A61M 16/109 128/203.27 |
| 2015/0352299 A1 | 12/2015 | Cortez, Jr. et al. | |
| 2016/0001031 A1 | 1/2016 | Laing et al. | |
| 2016/0015926 A1* | 1/2016 | Hermez | A61M 16/0808 128/203.26 |
| 2016/0022948 A1* | 1/2016 | Martin | A61M 16/024 128/205.25 |
| 2016/0303342 A1 | 10/2016 | Dwyer et al. | |
| 2016/0310692 A1 | 10/2016 | Drew | |
| 2017/0266408 A1 | 9/2017 | Giovannelli et al. | |

FOREIGN PATENT DOCUMENTS

| | | |
|---|---|---|
| DE | 3730551 A1 | 3/1989 |
| DE | 4312793 A1 | 10/1994 |
| DE | 102009014746 A1 | 10/2010 |
| EP | 0672430 A2 | 9/1995 |
| EP | 2269680 A1 | 1/2011 |
| EP | 2283889 A2 | 2/2011 |
| JP | 63246176 A | 10/1988 |
| JP | 2018514301 A | 6/2018 |
| WO | 2007101298 A1 | 9/2007 |
| WO | 2009015410 A1 | 2/2009 |
| WO | 2015/196379 A1 | 12/2015 |
| WO | 2016036260 A1 | 3/2016 |
| WO | 2016176284 A1 | 11/2016 |

OTHER PUBLICATIONS

"Mu-Metal Alloy for Fabricated Shield," Magnetic MuMetal Shield Corp., p. 2—Typical Magnetic Properties, May 2014.

* cited by examiner

SYSTEM AND METHOD FOR ON-DEMAND NEAR-PATIENT HUMIDIFICATION

CROSS-REFERENCE TO RELATED APPLICATION

This application claims priority to U.S. provisional patent application No. 62/413,154, filed Oct. 26, 2016, the disclosure of which is incorporated by reference herein in its entirety.

TECHNICAL FIELD

The present disclosure generally relates to a system and method for providing on-demand near-patient humidification to a respiratory breathing circuit, and more particularly, to a system and method for providing simultaneous independent control of temperature and humidity of a breathing gas.

BACKGROUND

Humidification during mechanical ventilation is often necessary to reduce drying of a patient's airways in order to prevent patient discomfort and possible complications, such as inspissation of airway secretions, hypothermia, and atelectasis. While passive humidifiers can provide some relief, generally a heated humidifier is required to maintain proper temperature and moisture of air delivered to a patient.

Conventional methods for humidifying gas often utilize a water chamber. The water chamber holds a quantity of water that is heated using a heating element. Dry gas is fed into the chamber and is humidified with the heated water. The humidified gas then exits the chamber and is delivered to a breathing circuit connected to the patient. Unfortunately, these conventional heating elements can often be bulky and must be located away from patient. This arrangement can be cumbersome and can also lead to the formation of condensation in the breathing circuit.

For example, such conventional humidification systems supply heat and humidity to respiratory gasses at an end of the breathing circuit near a ventilator. Such an arrangement adds energy in the form of heat to water within a reservoir, causing the water to evaporate and be transferred to the patient via the respiratory airflow. However, predictive control of humidity to a predetermined target, goal, or setting is not permitted in such conventional systems due to the variability of delivered humidity levels in an inspiratory gas flow resulting from cooling and condensation of vapor in the breathing circuit.

Most medical applications require airflow temperature to exceed ambient temperature, resulting in conditions that permit vapor condensation on the inner walls of the breathing circuit. However, conventional humidifiers allow the operator to grossly alter the humidity level by adjusting the reservoir temperature and the gas temperature within the breathing circuit by using heated wires. International standard ISO 8185 specifies that respiratory gasses should be humidified to a minimum absolute humidity of 33 g/m³ at 37° C. While such conventional humidification systems may meet minimum requirements, they are not capable of controlling the absolute humidity. Moreover, such conventional humidification systems may be able to adjust, but not control, the relative humidity (RH) between the minimum humidity and fully saturated air (i.e., at 100% RH).

Accordingly, there is a need for an improved humidification system and method that can provide on-demand near-patient humidification for respiratory breathing circuits. Furthermore, there is a need for a humidification system and method that permits simultaneous independent control of the temperature and humidity of an inspiratory airflow of a medical respiratory ventilation circuit.

SUMMARY

The foregoing needs are met, to a great extent, by implementations of the system and method for on-demand near-patient humidification according to the present disclosure. The present disclosure further provides a method, process, or algorithm for controlling vapor administered to a patient. Further, the system and method for on-demand near-patient humidification according to the present disclosure in treatments utilizing high continuous flow, oscillating ventilators, non-invasive masks, or other myriad treatments. In accordance with one implementation, the near-patient humidification system for providing vapor to a respiratory breathing circuit comprises an expiratory gas conduit, an inspiratory gas conduit, a patient coupling member, a vapor injection unit, and a vent coupling member. The expiratory gas conduit is configured to transport an expiratory gas flow from a patient. The inspiratory gas conduit is configured to transport an inspiratory gas flow to a patient. The patient coupling member is configured to couple the expiratory and inspiratory gas conduits to a patient interface. The patient coupling member has a housing defining an expiratory gas passage in communication with the expiratory gas conduit, an inspiratory gas passage in communication with the inspiratory gas conduit, a proximal end having an expiratory gas outlet and at least one inspiratory gas inlet, and a distal end having an expiratory gas inlet and an inspiratory gas outlet. The vapor injection unit is located at least partially within the housing of the patient coupling member, and includes a heater assembly configured to heat a supply of fluid into vapor and to inject the vapor into the inspiratory gas passage of the patient coupling member at a vapor injection location for providing humidity to the inspiratory gas flow.

According to one aspect of the disclosure, the vapor injection unit comprises a vapor housing having a proximal end and a distal end, the vapor housing defining a housing lumen extending from the proximal end to the distal end. The vapor injection unit may further comprise a cannula defining an inner lumen configured to receive a flow of water, and wherein the inner lumen is in fluid communication with the inspiratory gas passage of the patient coupling member.

According to another aspect of the disclosure, the heater assembly may be an induction heater assembly or a conduction heater assembly. In the induction heater assembly, and the vapor injection unit may comprise an induction element surrounding at least a portion of the cannula. The induction element may comprise at least one helically wound metallic coil. The induction element may comprise one or more electrical conductors configured to generate an oscillating magnetic dipole. The induction element may comprise at least two electrical conductors configured to generate an oscillating magnetic multipole. Further, the at least two electrical conductors may be wires or a printed circuit.

According to another aspect of the disclosure, the near-patient humidification system may comprise a heating element located inside the cannula and be at least partially surrounded by the induction element; wherein the induction element is configured to be excited by electrical current supplied from a power assembly, to generate an oscillating magnetic field to create eddy currents in the heating element to heat the heating element, and thereby heat the flow of water in the cannula flowing past the heating element, to thereby vaporize the water into steam which exits the vapor injection unit to be injected into the inspiratory gas passage. The heating element may comprise Mu-metal. Further, the heating element may include a magnetic material with a relative magnetic permeability greater than one. Further, the heating element may comprise a rolled foil spirally disposing a plurality of layers of said foil. In another aspect, the heating element may comprise a wire mandrel and a foil wrapped around the wire mandrel in a spiral pattern disposing a plurality of layers of said foil.

According to another aspect of the disclosure, the housing includes a proximal end configured to releasably engage the expiratory and inspiratory gas conduits, and a distal end configured to releasably engage a patient interface. The system may further comprise a vent coupling member adapted to releasably couple the expiratory and inspiratory gas conduits to a ventilator. Further, the expiratory and inspiratory gas conduits may be concentrically arranged, such that the expiratory gas conduit defines an inner conduit and the inspiratory gas conduit defines an outer conduit. The expiratory gas conduit may be configured to permit moisture to permeate through walls of the expiratory gas conduit so that humidity or water vapor in the expiratory gas flow can be transferred to the inspiratory gas flow in the inspiratory gas conduit.

According to another aspect of the disclosure, the system may comprise a first sensor configured to independently measure a temperature and/or humidity of the inspiratory gas flow at a location upstream from the vapor injection location, and a second sensor configured to independently measure a temperature and/or humidity of the of the inspiratory gas flow at a location downstream from the vapor injection location. The first and second sensors may be spaced equally apart from the vapor injection location. The vapor injection unit may comprise a vapor housing having a proximal end and a distal end, the vapor housing defining a housing lumen extending from the proximal end to the distal end, and wherein the vapor injection unit includes a hub connected to the proximal end of the vapor housing and being configured to connect to a fluid supply. A check valve may be provided proximal to the heated element.

According to another aspect of the disclosure, the vapor injection unit may comprise a vapor housing having a proximal end and a distal end, the vapor housing defining a housing lumen extending from the proximal end to the distal end, and wherein the vapor housing comprises a thermally insulating material. The vapor injection unit may comprise a vapor housing having a proximal end and a distal end, the vapor housing defining a housing lumen extending from the proximal end to the distal end; wherein the vapor injection unit further comprises a cannula defining an inner lumen configured to receive a flow of water; wherein the inner lumen is in fluid communication with the inspiratory gas passage of the patient coupling member; and wherein the cannula is made from a material selected from a metal, plastic, glass, ceramic, and a combination thereof.

According to another aspect of the disclosure, the vapor injection unit may comprise a power assembly for connection to an electrical power source. The power assembly may be located at the proximal end of the vapor housing.

The present disclosure also provides a method of simultaneously and independently controlling the temperature and humidity of inspiratory gas in a respiratory breathing circuit comprises the steps of providing a near-patient humidification system; supplying a breathing gas to the respiratory breathing circuit; measuring a first temperature and a first humidity of the breathing gas at a location upstream from a vapor injection unit; measuring a second temperature and a second humidity of the breathing gas at a location downstream from a vapor injection unit; and injecting vapor from the vapor injection unit into the respiratory breathing circuit, the vapor having a vapor temperature determined as a function of the measured first and second temperatures and the measured first and second humidities of the breathing gas.

In another implementation of the present disclosure, a heating element for a humidification device to heat a fluid flowing through the device comprises a mandrel core, a rolled foil spirally wrapped around the mandrel core to dispose a plurality of layers of said foil around the mandrel core; and a plurality of gaps formed between adjacent layers of wrapped foil and configured to provide a tortuous pathway for the fluid to travel in order to transfer heat from the foil to the fluid. In some aspects, the mandrel core may be a wire or a rod. Further, at least one of the mandrel core and the rolled foil may comprise a magnetic material. The magnetic material may be selected from the group consisting of Mu-metal, Alumel, nickel, iron, and permalloy. The rolled foil spirally wrapped around the mandrel core may comprise a jelly roll shape. The rolled foil may further comprise at least three or four adjacent layers. The rolled foil spirally wrapped around the mandrel core may further comprise a spiral cross-section.

Certain aspects of the system and method for on-demand near-patient humidification have been outlined such that the detailed description herein may be better understood. It is to be understood that the humidification system and method are not limited in application to the details of construction and to the arrangements of the components set forth in the following description or illustrated in the drawings. The humidification system and method is capable of aspects in addition to those described, and of being practiced and carried out in various ways. Also, it is to be understood that the phraseology and terminology employed herein, as well as in the Abstract, are for the purpose of description and should not be regarded as limiting.

As such, the conception upon which this disclosure is based may readily be utilized as a basis for the designing of other structures, methods, and systems for carrying out the several purposes of the humidification system and method. It is understood, therefore, that the claims should be regarded as including such equivalent constructions insofar as they do not depart from the spirit and scope of the present disclosure.

BRIEF DESCRIPTION OF THE DRAWINGS

In order that the disclosure may be readily understood, aspects of the humidification system and method are illustrated by way of examples in the accompanying drawings.

Implementations of the humidification system and method are described with reference to the drawings, in which like reference numerals refer to like parts throughout.

DETAILED DESCRIPTION

The present disclosure is directed to a respiratory humidification system and method for on-demand near-patient humidification. The respiratory humidification system may comprise a humidification device configured to add moisture to a breathing gas in order to a control a humidity level thereof. As used herein, a "breathing circuit" or "breathing gas circuit" may be any arrangement of tubes or conduits which carries gases to be administered to and from a patient, such as from a ventilator, and which may include additional accessories or devices attached thereto. Such "breathing gases" may include oxygen, air or any component thereof, and are configured to absorb high levels of moisture and/or be humidified prior to administration to a patient, or during administration to a patient, and be suitable for medical applications.

Figure 1:
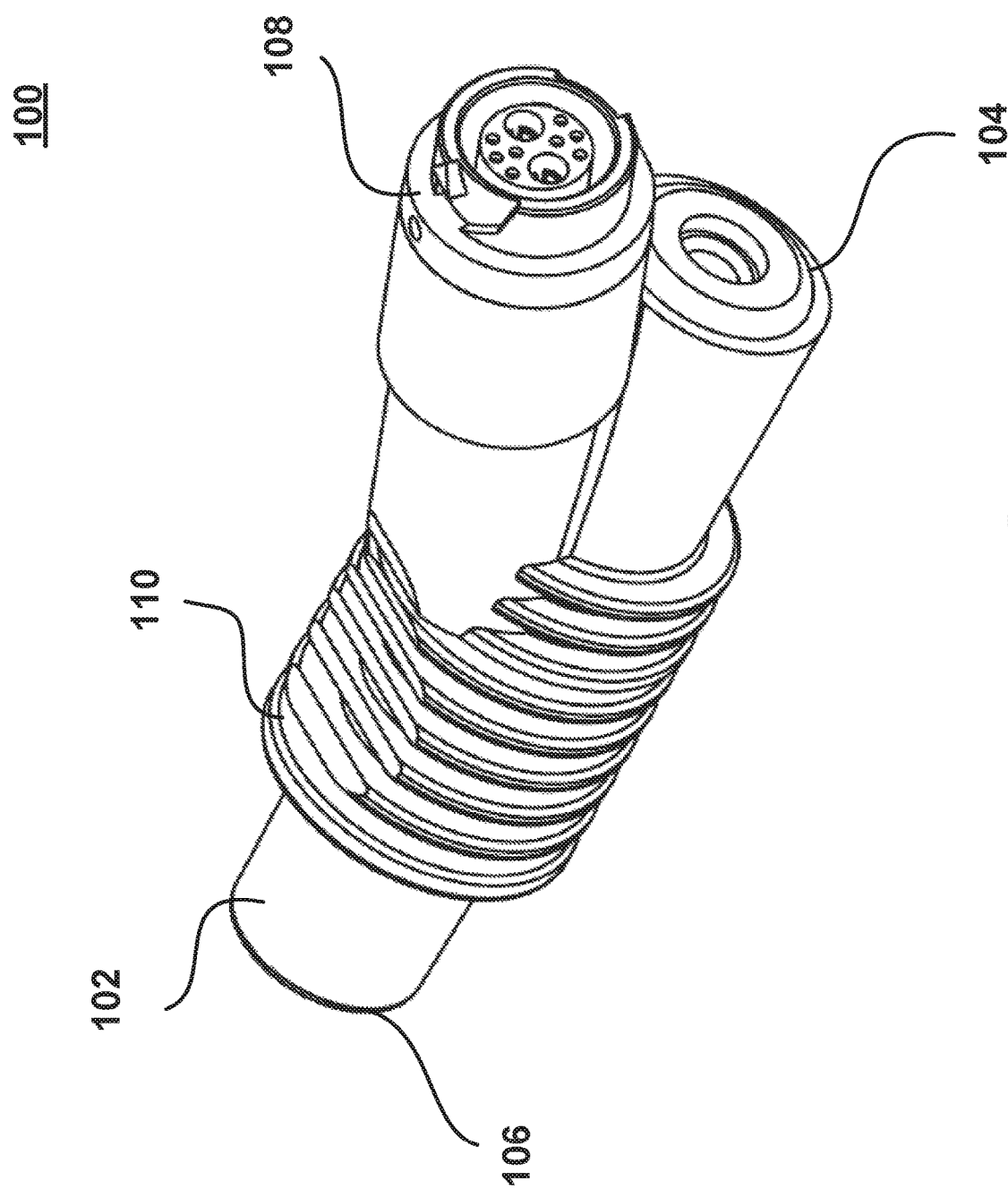
FIG. 1 is a perspective view of an induction heater assembly of a humidification system according to a first implementation of the disclosure.

One implementation of the humidification device may include a heater assembly 100 and a heating element assembly 200. The heater assembly 100 may be an induction heater assembly in some implementations, or alternatively, a conduction heater assembly in other implementations. For instance, such an heater assembly 100 that forms part of the humidification device is illustrated in FIG. 1. The heater assembly 100 may include a housing 102 having a proximal end 104 and a distal end 106. The heater assembly 100 may also include a power and controls interface assembly 108 connected to the housing 102. A plurality of cooling fins 110 may extend from a portion of the housing 102 and the power and controls interface assembly 108. In some aspects, the cooling fins 110 may extend from a portion of the housing 102 and the power and controls interface assembly 108.

Figure 2:
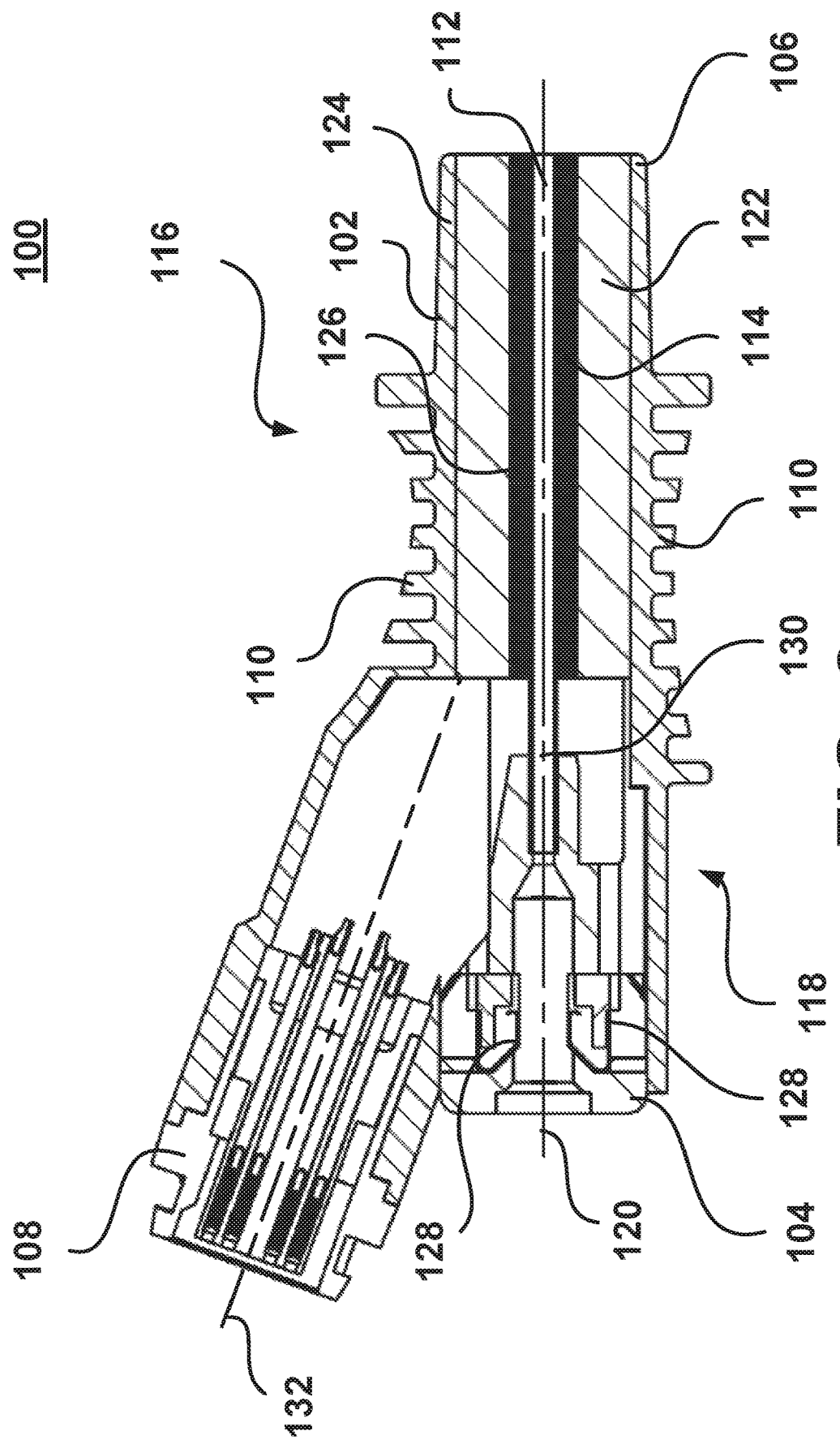
FIG. 2 is a cross-sectional view of the induction heater assembly of the humidification device of FIG. 1.

FIG. 2 illustrates a cross-sectional view of the heater assembly 100 of FIG. 1. The housing 102 may define a housing lumen 112. The housing lumen 112 may extend from the proximal end 104 to the distal end 106. The housing lumen 112 may be configured to receive a heating element assembly 200 (shown in FIG. 4) at the proximal end 104. The shape of the housing lumen 112 may match the shape of the heating element assembly 200. For example, the diameter of the housing lumen 112 may be greater towards the proximal end 104 than the diameter of the housing lumen 112 at the distal end. According to another aspect of the disclosure, the heating element assembly 200 may be disposable.

The heater assembly 100 may include an induction element 114 located along the housing lumen 112. The induction element 114 may be located at a distal region 116 opposite from a proximal region 118 of the housing lumen 112. In other aspects, the induction element 114 may span from the distal region 116 to the proximal region 118 of the housing lumen 112. In some aspects, the induction element 114 may be an induction coil formed from a single or multiple enameled wires. If the induction element 114 is formed from multiple wires, the multiple wires may be twisted to form a Litz wire. A Litz wire configuration can reduce power loss and heat generated by the "skin effect" at high alternating current (AC) frequencies. The induction element 114 may be center-tapped, and a positive voltage may be supplied at the center tap. The ends of the induction element 114 may be alternately switched to ground to generate an oscillating magnetic field within the interior of the induction element 114. The oscillating magnetic field created from the induction element 114 may produce eddy currents to heat objects placed within the housing lumen 112. It should further be appreciated that the induction element may comprise a rectangular cross-section magnet wire which provides similar results as the aforementioned Litz wire. Further, according to another aspect, power to the induction element 114 may be switched to ground, or between positive and negative voltages. The voltage waveform may be square for providing most efficiency, sinusoidal for minimizing EMI, or another waveform such as triangular or sawtooth.

In other aspects, the induction element 114 may be a pair of parallel electrical conductors configured to generate a dipole. The pair of parallel electrical conductors may extend within the housing lumen 112 parallel to a center axis 120. The pair of parallel electrical conductors may be insulated wires or conductive tracks formed onto a flexible printed circuit. The printed circuit may be formed to fit into the housing lumen 112 of the heater assembly 100. For example, in the aspect shown in FIG. 2, the induction element 114 as a printed circuit may be shaped like a hollow cylinder. To generate a dipole, a positive voltage may be supplied to one of the electrical conductors. The two ends of the other electrical conductor may be alternately switched to ground at a high frequency in order to generate an oscillating magnetic field within the housing lumen 112.

In further aspects, the induction element 114 may be more than two pairs of electrical conductors configured to generate an oscillating magnetic field having multiple poles, such as a quadrupole, hexapole, octupole, or another multipole system with either an even or odd number of magnetic poles. The pairs of electrical conductors may similarly extend within the housing lumen along the center axis 120. The electrical conductors may be insulated wires or conductive tracks formed onto a flexible printed circuit board. A positive voltage may be supplied to one set of electrical conductors. The set of electrical conductors may be alternately switched to ground at a high frequency to create a rapidly oscillating magnetic field. In other aspects, a circuit may be used to switch the polarity of each end of the induction element 114 to improve the efficiency of the induction element 114.

In the various aspects described above, the induction element 114 may generate an oscillating magnetic field with frequencies between up to 200 kHz. In further aspects, electromagnetic shielding, specifically radio frequency shielding, may be necessary such that the heater assembly 100 meets various regulatory electro-magnetic emission requirements.

As mentioned previously, a plurality of cooling fins 110 may extend from a portion of the housing 102. In other aspects, the cooling fins 110 may also extend from an exterior surface of the power and controls interface assembly 108. The cooling fins 110 may increase the rate of heat transfer from the heater assembly 100 by increasing the amount of surface area of the heater assembly 100 exposed to the air. In some aspects, the cooling fins 110 may be used to transfer heat from the induction element 114 into the gas flow stream by extending into the gas flow line. In some aspects, the cooling fins 110 may be made from the same material as the housing 102. In other aspects, the cooling fins may be made from material with a greater heat transfer coefficient than that of the material for the housing 102 in order to improve the cooling abilities of the cooling fins 110. The plurality of cooling fins 110 may have a circular, square, elliptical, rectangular, or other similar shape. The shape and size of the cooling fins 110 may be the same or may vary among the plurality of cooling fins 110. For instance, the cooling fins may be any shape intended to reduce external surface temperatures that may contact the patient or user.

The heater assembly 100 may also include a thermal insulator 122. The thermal insulator 122 may be located between the induction element 114 and the inner surface 124 of the housing 102. The thermal insulator 122 may extend radially from the outer surface 126 of the induction element 114. The thermal insulator 122 may be made from a material with low thermal conductivity to reduce heat transfer away from the induction element 114, which may increase the transfer of heat generating by the induction element 114 through the housing lumen 112 and cannula 202 into the fluid. Materials for the thermal insulator 122 may include ceramics, glass, composite materials such as glass-bonded mica (Mykroy/Mycalex), fiberglass, insulating plastics, or other suitable materials. The thermal insulator 122 may be formed from extruded tubing or another process suitable to shape the thermal insulator 122 to fit within the housing 102. Alternatively, a thermally conductive material may be selected for the thermal insulator 122 to transfer heat from the induction element 114 towards the cooling fins 110 and/or into the respiratory gas.

The heater assembly 100 may include thermocouple electrical contacts 128 formed on an inner surface 124 of the housing 102. The thermocouple electrical contacts 128 may be configured to engage corresponding thermocouple conductors (shown in FIG. 4) on the heating element assembly 200. The thermocouple electrical contacts 128 may be formed at the proximal region 118 of the housing 102. The thermocouple electrical contacts 128 may be in electrical connection with the power and controls interface assembly 108. Once the heating element assembly 200 is received within the heater assembly 100 and the thermocouple electrical contacts 128 engage the corresponding exposed thermocouple conductor surfaces 218 and 220, an electrical circuit will be completed within the heater assembly 100. In other aspects, the heater assembly 100 may use other devices, such as thermistors or resistance temperature detectors (RTDs), to measure temperature.

The heater assembly 100 may also include a non-magnetic tube 130 within and at the proximal region of the housing lumen 112. The non-magnetic tube 130 may only extend a portion of the length of the housing lumen 112. The non-magnetic tube 130 may be configured to receive the heating element assembly 200. The non-magnetic tube 130 may prevent direct contact between the induction element 114 and the heating element assembly 200 once the heating element assembly 200 is received within the heater assembly 100. The spacing between the induction element 114 and the heating element assembly 200 may improve performance of the induction element 114. The non-magnetic tube 130 may be made from plastic, glass such as borosilicate glass, ceramics, heat-resistant plastics, or other suitable non-magnetic materials.

As shown in FIG. 2, the power and controls interface assembly 108 is connected to the housing 102. The power and controls interface assembly 108 and housing 102 may be a single component. The power and controls interface assembly 108 may be implemented as a connector receptacle or other interface to facilitate a quick connection and/or disconnection with an electrical power source and/or control interface. In other aspects, the power and controls interface assembly 108 may include an electrical power source and be removably coupled to the housing 102. The power and controls interface assembly 108 may provide electrical power to the induction element 114 and/or thermocouple electrical contacts 128. The electrical connection may be established using insulated wires and/or flexible printed circuits. The power and controls interface assembly 108 may be oriented along a power assembly axis 132. In the aspect shown in FIG. 2, the power assembly axis 132 may be at an acute angle to the center axis 120 of the housing 102. In other aspects, the power assembly axis 132 may be at any angle perpendicular or parallel to the center axis 120.

Figure 3:
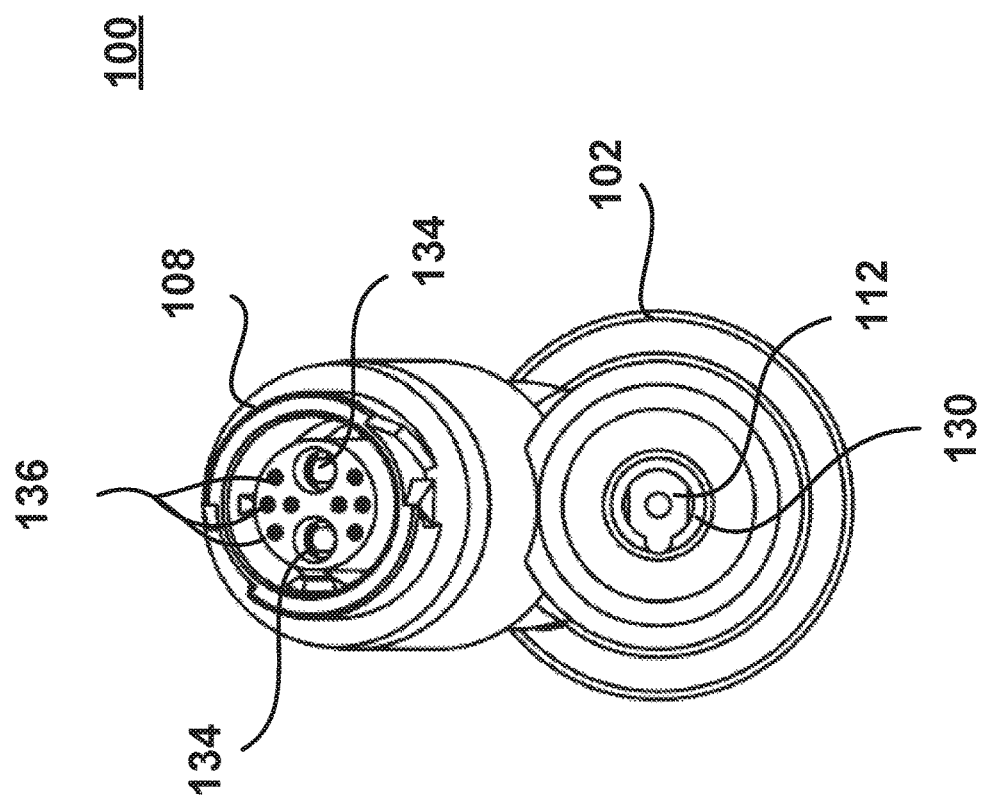
FIG. 3 is a front view of the induction heater assembly of the humidification device of FIG. 1.

FIG. 3 illustrates a front view of a heater assembly 100. The power and controls interface assembly 108 may have a plurality of electrical contacts 134 to engage an electrical power source (not shown). The electrical contacts 134 may provide electrical power to the thermocouple contacts 128. The power and controls interface assembly 108 may also include a plurality of electrical pins 136. The electrical pins 136 may be used to facilitate an electrical connection with an electrical power source and/or control interface.

Figure 4:
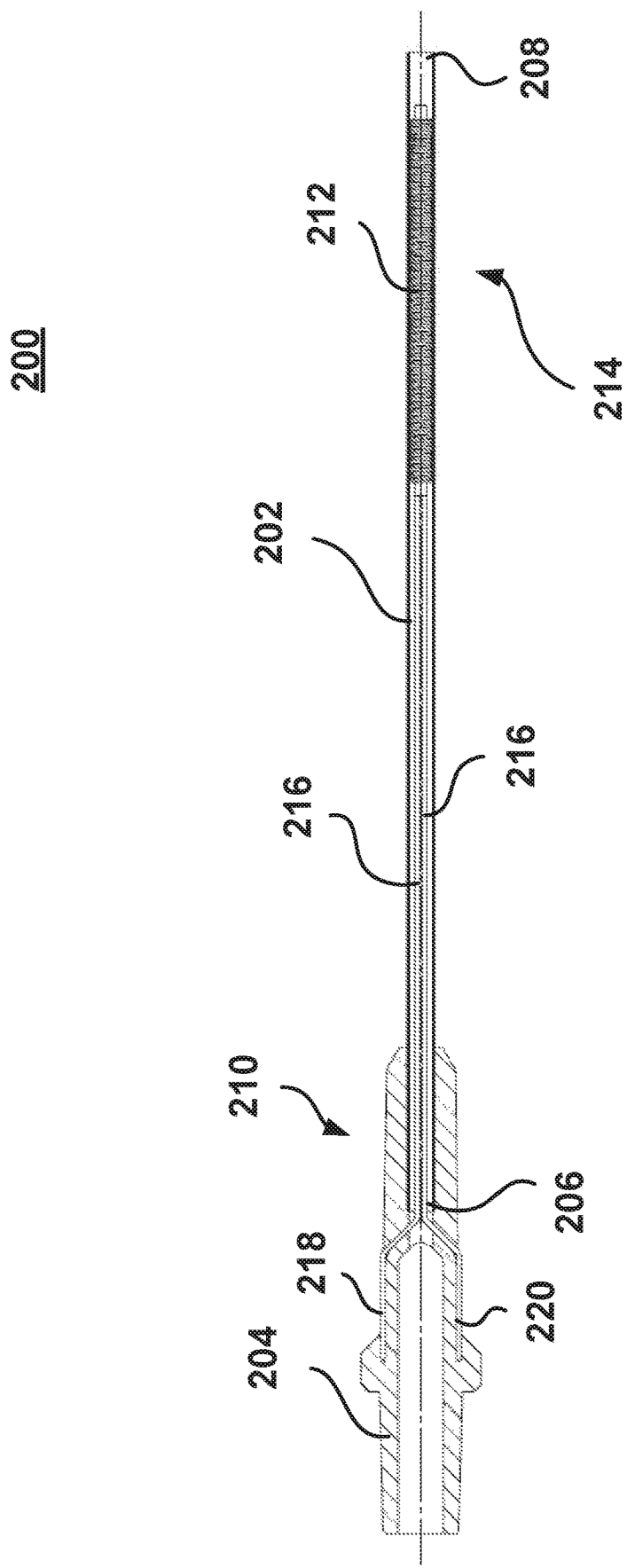
FIG. 4 is a cross-sectional view of a heating element assembly of the humidification device according to an aspect of the disclosure.

FIG. 4 illustrates a heating element assembly 200 that forms another part of the humidification device according to one implementation for use in the humidification system of the present disclosure. The heating element assembly 200 includes a cannula 202 connected to a hub 204. The cannula may be a tube configured to be removably received within the non-magnetic tube 130 and/or housing lumen 112 of the heater assembly 100. The cannula 202 may be made from materials such as stainless steel, glass, ceramic, or other suitable materials. The cannula 202 may be magnetic or non-magnetic. The cannula 202 may extend between a proximal end 206 and a distal end 208. The proximal end 206 may be connected to the hub 204 while the distal end 208 may be configured to be inserted into the housing lumen 112 of the heater assembly 100. The hub 204 may be formed around a portion of cannula 202 in an overlapping region 210. The hub 204 may have a standardized Luer connection or a custom connection.

The heating element assembly 200 may include a heating element 212 located within the cannula 202. The heating element 212 may be made from a magnetic material such as Mu-metal, Alumel, nickel, iron, permalloy, or other materials with a high relative magnetic permeability. The heating element 212 may be a tube, a solid cylinder such as a rod or wire, a matrix of cylinders, a sintered cylinder, a porous cylinder, a sheet, a spiral sheet, a coil, or any combination of the foregoing. It should also be appreciated that the heating element 212 may comprise a rolled foil having a jelly roll shape, as will be described in greater detail below. As illustrated in FIG. 4, the heating element 212 may be a twisted or helical coil of multiple wires. The heating element 212 may be located at a distal region 214 of the cannula. In other aspects, the heating element 212 may extend from the proximal end 206 to the distal end 208.

The heating element 212 may be configured to overlap with the induction element 114 when the heating element assembly 200 is removably received within the heater assembly 100. The heating element 212 may be configured to interact with the oscillating magnetic field generated by the induction element 114. The heating element 212 can have a high magnetic permeability because the efficiency of induction heating within the heating element 212 may be greater. The heating element 212 can have a greater surface area to increase the efficiency of heat transfer between the fluid pumped into the cannula and the heating element 212.

The heating element assembly 200 may include thermocouples conductors 216. The thermocouple conductors 216 may allow a user to monitor and/or provide closed-loop temperature control of the heating element 212. The thermocouple conductors 216 may be integrated with the heating element 212 as a single component. In other aspects, the thermocouple conductors 216 may be a separate component from the heating element 212. As illustrated in FIG. 4, the thermocouple conductors 216 are separate components form the heating element 212 with the heating element 212 located at the distal region 214 of the thermocouple conductors 216. In other aspects, one of the thermocouple conductors 216 may be integrated into the cannula 202 and/or be placed in contact with the fluid path, which may allow the cannula 202 and/or a fluid to act as a conductor, such that at least a portion of the measured thermocouple voltage is measured across the cannula 202 and/or fluid.

One or both of the thermocouple conductors 216 may be made from a magnetic material, such as Mu-metal, Alumel, nickel, iron, permalloy, or another alloy, to allow the thermocouple conductors 216 to interact with the oscillating magnetic field generated by the induction element 114 and produce heat, which increases the efficiency of the heating element 212. The thermocouple conductors 216 may be made from the same material as the heating element 212 to simplify fabrication of the heating element assembly 200. In other aspects, at least one of the thermocouple conductors 216 may be made from a non-magnetic alloy to reduce generation of induction heating within the non-magnetic leg and improve accuracy of the temperature measurements. Non-magnetic materials may include copper, Nicrosil, Nisil, Chromel, Constantan, or other similar alloys. A material with low thermal conductivity for the non-magnetic leg can further improve accuracy.

The thermocouple conductors 216 may correspond to a positive electrode and a negative electrode. The voltage differential between the thermocouple conductors 216 may vary depending on the temperature, which may be used to determine and control the temperature of the heating element assembly 200. The thermocouple conductors 216 may have exposed thermocouple conductor surfaces 218 and 220. The exposed thermocouple conductor surfaces 218 and 220 may be located on a surface the hub 204. The exposed thermocouple conductor surfaces 218 and 220 may be configured to engage the thermocouple electrical contacts 128 on the heater assembly 100 once the heating element assembly 200 is received within the housing 102 to allow the voltage to be read.

For operation of the humidification device, the heating element assembly 200 may be inserted into the housing 102 of the heater assembly 100. The induction element 114 may be excited to generate an oscillating magnetic field, which may create eddy currents within the heating element 212. The eddy currents generated in the heating element 212 may heat the heating element 212. Water may be pumped into the heater assembly 100 at the proximal end 104 and through the cannula 202 of the heating element assembly. As water travels past the heating element 212, the water may rapidly absorb heat and vaporize into steam. As steam forms, the rapid expansion may cause pressurized steam to be injected into a patient's breathing circuit gas conduit and humidify the gases. The steam pressure may also apply force against the supply water. The process may repeat in a cyclical fashion resulting in steam periodically injected into the patient's breathing circuit.

Although the humidification device may include the heater assembly 100 and the heating element assembly 200 as separate units as shown in FIGS. 2 and 4, in other aspects, the heater assembly 100 and the heating element assembly 200 may be combined to form a single integral unit. For example, the heating element 212 and thermocouple conductors 216 may be integrated into the heater assembly 100 to form the humidification device. The combined heater assembly 100 and heating element assembly 200 may be designed to be disposable and/or replaceable after a limited number of uses. Further, in other implementations of the disclosure, the heating element 212 may be a conduction heating element configured to be heated by conduction.

Figure 5:
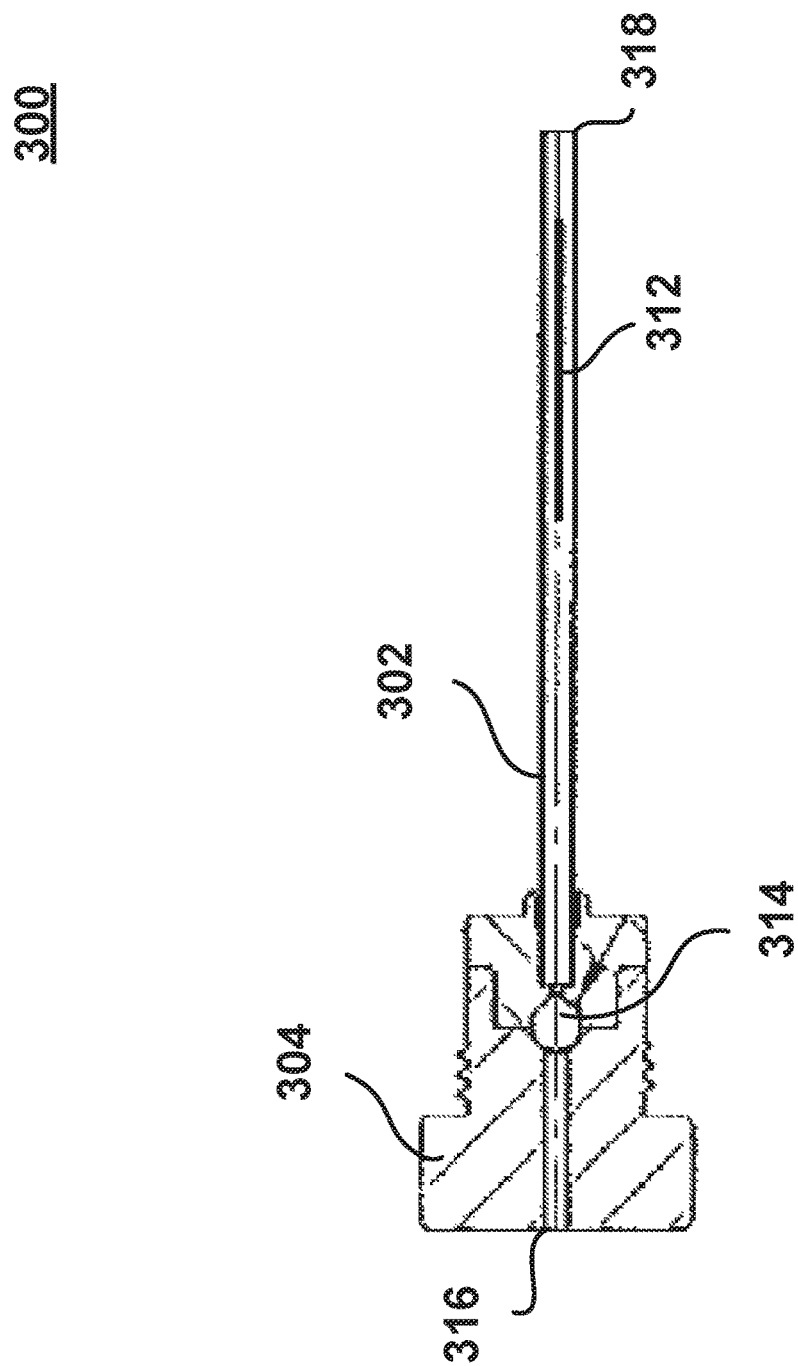
FIG. 5 is cross-sectional view of another implementation of a heating element assembly of a humidification device.

FIG. 5 illustrates another implementation of the heating element assembly 300 that forms part of a humidification device according to another aspect of the disclosure. The heating element assembly 300 is similarly configured to be removably received within the housing 102 of the heater assembly 100. The heating element assembly may include a cannula 302, hub 304, and heating element 312 similar to the aspects described above with respect to FIG. 4. In addition, the heating element assembly 300 may include a check valve 314. The check valve 314 may be a valve that only permits fluid to flow from the proximal end 316 to the distal end 318. The check valve 314 may be implemented with at least one of a ball check valve, a diaphragm check valve, a swing check valve, a stop-check valve, a pneumatic non-return valve, or another similar mechanical valve. The check valve 314 may close the supply of water entering the heating element assembly 300 as a result of steam pressure formed within the heating element assembly 300.

Figure 6:
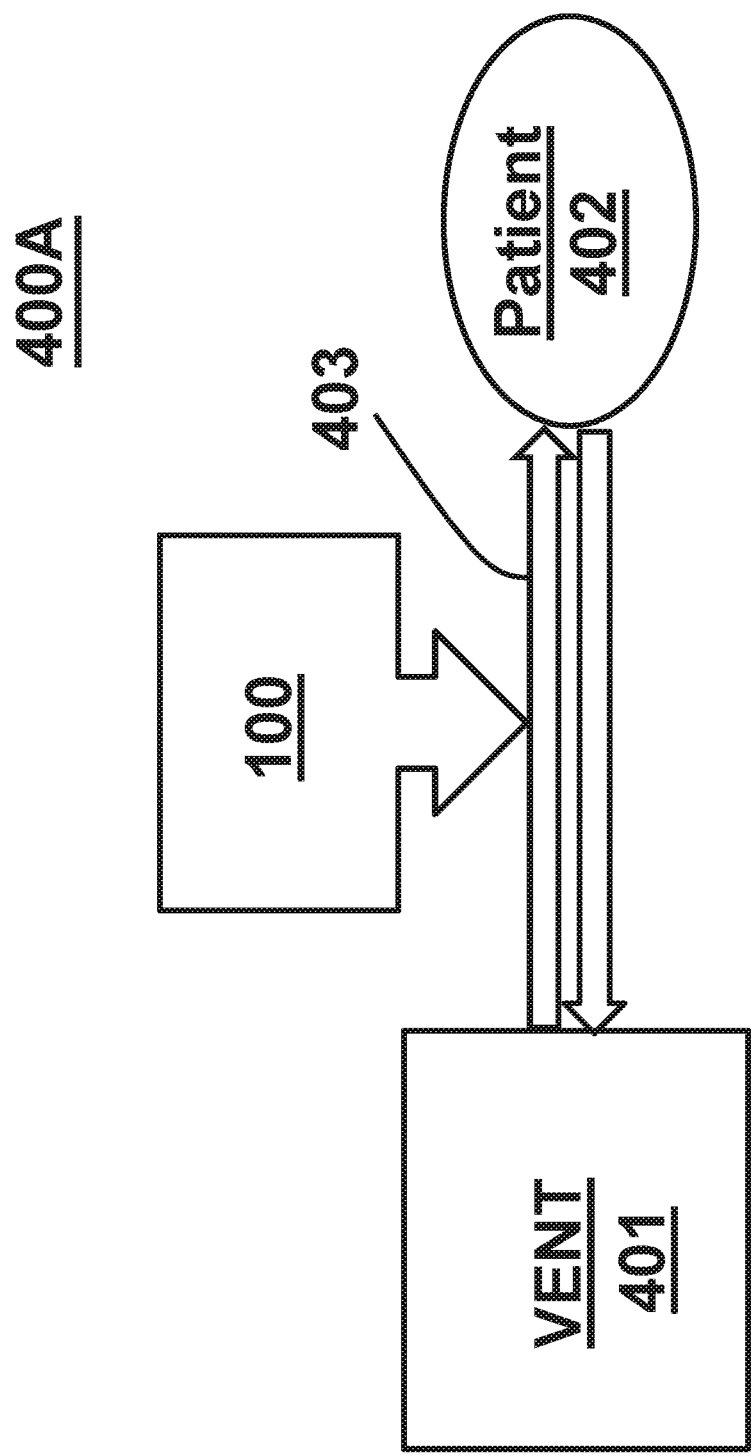
FIG. 6 is schematic system diagram of a humidification device of the disclosure coupled to a respiratory breathing circuit.

FIG. 6 is a schematic diagram illustrating a standard respiratory system 400A that includes a ventilator 401 and a patient or patient interface 402, which are fluidly interconnected by a respiratory breathing circuit 403, as is known in the art. In the standard respiratory system 400A, an embodiment of the humidification device having the heater assembly 100 may be coupled to the respiratory breathing circuit 403 so that steam may be injected into a patient's breathing circuit gas conduit at some point along the respiratory breathing circuit 403, to thereby humidify the gases flowing therein, and deliver the humidified gas to the patient or patient interface 402.

Figure 7:
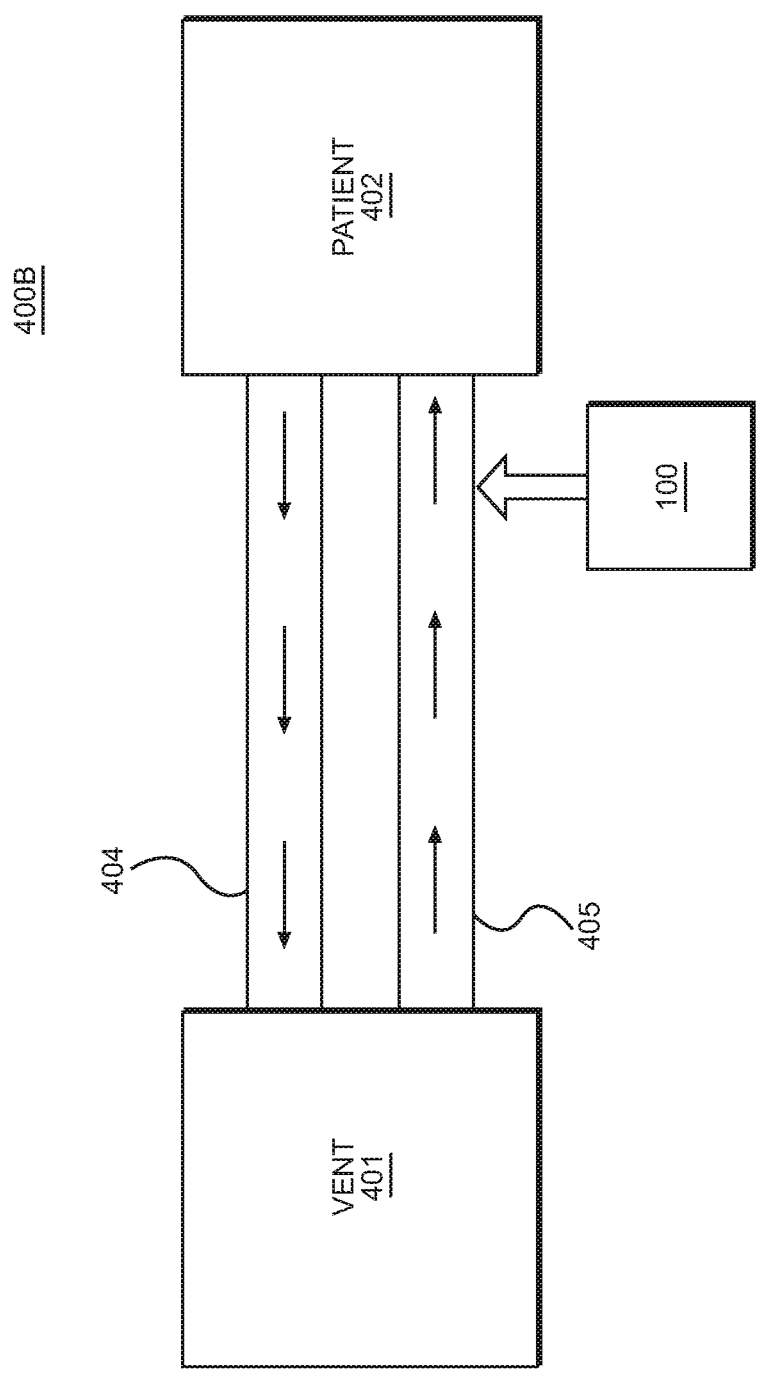
FIG. 7 is a schematic diagram of a multi-limb humidification system according to another implementation of the disclosure.

FIG. 7 is a schematic diagram illustrating an implementation of a multi-limb respiratory humidification system 400B for on-demand near-patient humidification according the present disclosure, wherein the respiratory breathing circuit comprises at least one expiratory limb 404 defining an expiratory gas conduit configured to transport expiratory gas from the patient 402 to the ventilator 401, and at least one inspiratory limb 405 defining an inspiratory gas conduit configured to transport inspiratory gas from the ventilator 401 to the patient 402. The at least one expiratory limb 404 and the at least one inspiratory limb 405 of the multi-limb system may be separate and spaced apart from each other. In one aspect, the expiratory and inspiratory conduits may be non-concentric. Further, in the multi-limb respiratory humidification system 400B, an embodiment of the humidification device of the present disclosure having the heater assembly 100 may be coupled to the inspiratory limb 405 at a location proximate the patient 402 so that steam may be injected into a dry breathing gas at a location near the patient to thereby humidify the breathing gas, and efficiently deliver the humidified gas to the patient.

In another implementation of a multi-limb respiratory humidification system for on-demand near-patient humidification according the present disclosure, the at least one expiratory limb 404 and/or the at least one inspiratory limb 405 of the respiratory breathing circuit may comprise a moisture removal and condensation and humidity management apparatus as described in U.S. Patent Publication No. 2016/0303342, which is hereby incorporated herein by reference, in order to remove or decrease water vapor, moisture, or condensate from the respective gas conduit.

Figure 8:
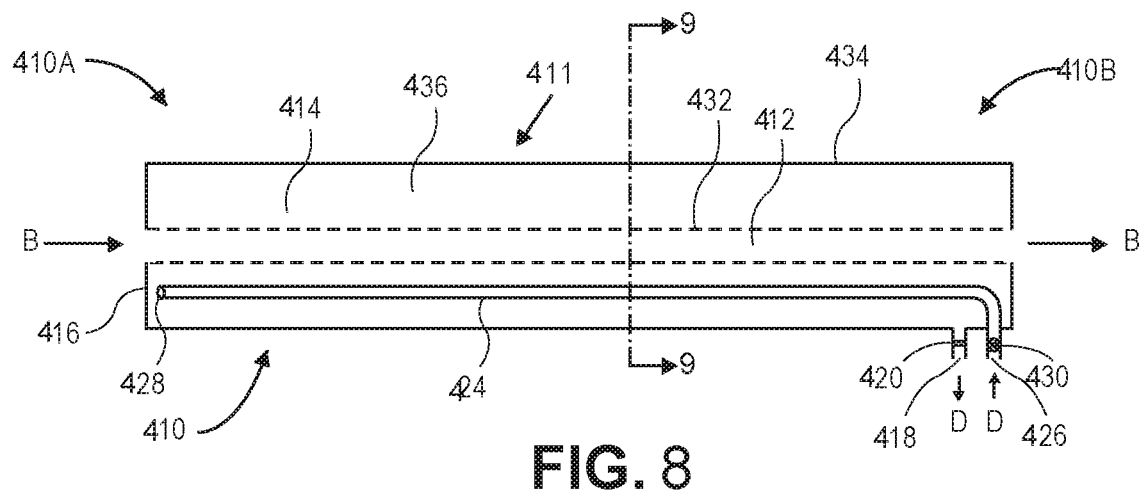
FIG. 8 is a schematic view illustrating an apparatus that may be incorporated into or as part of a breathing gas circuit in accordance with one or more implementations of the present disclosure.

It should be appreciated that the at least one expiratory or inspiratory limb 404, 405 of the respiratory breathing circuit may comprise other embodiments of the moisture removal and condensation and humidity management apparatus. For example, FIG. 8 is schematic view showing one embodiment of a moisture removal and condensation and humidity management apparatus 410 configured to rapidly remove water vapor or condensate from a humidified medical gas traveling therethrough. The moisture removal and condensation and humidity management apparatus 410 for a breathing circuit may include a section or length of breathing circuit tubing 411 defining a breathing gas conduit 412 for a flow (B) of breathing gas therein. The breathing gas flows from a first, upstream end 410A of the apparatus 410 proximate to a patient, through the breathing gas conduit 412 defined within the apparatus 410, and to a second, downstream end 410B of the apparatus 410 distal of the patient. The breathing gas may have a first humidity level and a level of moisture therein, which may be calibrated by the user based on the needs of the patient. In some embodiments, the length of breathing circuit tubing 411 is in an expiratory limb of a breathing circuit, for example, positioned somewhere between a patient and a ventilator.

The apparatus 410 may also include a dry gas conduit 414 adjacent to at least a portion of the breathing gas conduit 412 between the upstream end 410A and downstream end 410B, for a dry gas flow (D) therein. The dry gas flow (D) is configured to have a second humidity level which is lower than the first humidity level within the breathing gas conduit (B). In some embodiments, the dry gas conduit 414 may extend the entire length of the breathing gas conduit 412 to optimize moisture transfer. However, in some embodiments, the dry gas conduit 414 may extend less than the entire length of the breathing gas conduit 412. The dry gas conduit 414 may include a closed end 416 on the upstream end 410A, and downstream end 410B an outlet 418 at the downstream end 410B. The outlet 418 may be in communication with a source of suction and/or the ambient environment around the apparatus 410. In some embodiments, the outlet 418 may be in communication with a filter 420.

The apparatus 410 may further include a feeding conduit 424 configured to supply dry gas to the dry gas conduit 414. As depicted in FIG. 8, the feeding conduit 424 may include an inlet 426 at the downstream end 410B of the apparatus 410, and an outlet 428 at the first end 410B of the apparatus 410, such that the feeding conduit 424 extends through at least a portion of the dry gas conduit 414. For example, the feeding conduit 424 may extend greater than half of the length of the dry gas conduit 414. In some embodiments, the feeding conduit 424 may extend substantially the entire length of the dry gas conduit 414. Advantageously, the feeding conduit 424 may allow the inlet 426 and outlet 418 for dry gas of the apparatus 410 to be further away from the patient, reducing any potential safety risk to the patient. This prevents any potential sparking caused by the ingress and egress of the dry gas proximate the patient. Furthermore, by providing the outlet 418 of the feeding conduit 424 at the upstream end 410A within the dry gas conduit 414, the apparatus 410 may provide a large surface area for moisture/humidity transfer from the breathing gas conduit 412 to the dry gas conduit 414. In some embodiments, a flow or volume control element 430 (e.g., a valve) may be connected to the inlet 426 of the feeding conduit 424 and configured to control the flow of dry gas into the feeding conduit 424.

Figure 9:
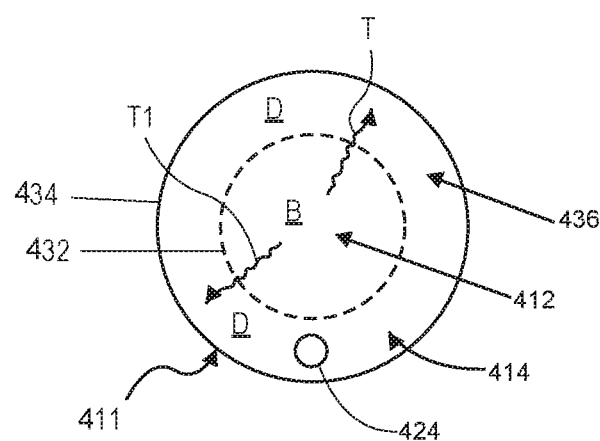
FIG. 9 is a schematic cross-sectional view taken along line 9-9 of FIG. 8.

FIG. 9 is a schematic cross-sectional view illustrating the apparatus 410 of FIG. 8 of one or more embodiments of the present disclosure. As shown in the embodiment of FIGS. 8-9, the dry gas conduit 414 may be an annular flow space which is concentric with breathing gas conduit 412. For example, the breathing circuit tubing 411 may include an inner tube 432 defining the breathing gas conduit 412, and an outer sleeve or tube 434 surrounding the inner tube 432 and defining the dry gas conduit 414. The dry gas conduit 414 thereby may include an annular conduit 436 defined between the inner tube 432 and outer tube 434. Alternatively, in some embodiments, the inner tube 432 may define the dry gas conduit 414 and the annular conduit 436 between the inner tube 432 and the outer tube 434 may include the breathing gas conduit 412. As depicted, the feeding conduit 424 may extend through the dry gas conduit 414. One or both, of the inner tube 432 and the outer tube 434 may include corrugated tubing. In the present disclosure, a moisture transmission pathway may be positioned between the breathing gas conduit 412 and the dry gas conduit 414. For example, a sufficient stretch of surface area of the breathing circuit tubing 411 may be shared between the breathing gas conduit 412 and the dry gas conduit 414 enabling transfer of moisture between the flow of breathing gas (B) and the flow of dry gas (D), as further described below.

The present disclosure provides one or more embodiments which provide the moisture transmission pathway between the breathing gas conduit 412 and the dry gas conduit 414, lowering the moisture and/or humidity in the flow of breathing gas (B) by transferring the moisture and/or humidity to the dry gas flow (D). For example, in FIG. 9, the moisture transmission pathway (T) may occur between the higher humidity breathing gases in breathing gas conduit 412 and the lower humidity dry gas flow in dry gas conduit 414. A user may increase or decrease the level of dry gas supplied to the dry gas conduit 414 to manage or remove the condensate which may be transferred from the breathing gas (B) to the dry gas (D). The moisture level thus may be reduced from within the breathing gas flow (B) and transferred to the dry gas flow (D).

In some embodiments, such as shown in FIG. 9, the breathing circuit tubing 411 may include a permeable portion or membrane (as depicted in broken lines) along part or all of the inner tube 432. The permeable portion may be permeable to water vapor but impermeable to liquid water, such that the moisture transmission pathway (T) is provided by the permeable portion of the breathing circuit tubing 411. The permeable portion may include one or more materials that are water vapor breathable and allow passage of water vapor, as is well known to those of ordinary skill in the art. The permeable portion may form some or all of the walls of the breathing gas conduit 412 (e.g., inner tube 432) and may include a single, or composite layer of water vapor breathable medium. For example, in some embodiments, the permeable portion may include an inner layer and an outer layer having different permeability/wicking properties. A first wicking layer may be provided as an inner layer of inner tube 432 and may be configured to contact the breathing gas flow (B) inside of the inner tube 432. The wicking layer may be made of one or more wicking materials that allow for adsorption and/or absorption of moisture and/or water in any phase (e.g., gas and/or liquid), for example, through capillary action. The permeable portion may also include an outer layer of water vapor breathable material that permits the passage of water vapor only, while not permitting passage of liquid water.

Examples of wicking material of the permeable portion include knitted and/or non-woven cloth or fabric. The wicking material may be natural and/or synthetic, such as polyester, polyester and polypropylene blends, nylon, polyethylene or paper. The wicking material may also include microfilaments and/or microfiber material such as Evolon® brand fabric material made by Freudenberg & Co. KG. One particular example of wicking material may be a non-woven material of 70% polypropylene and 30% polyester. Another example of the wicking material may be Evolon® brand fabric material having a weight of 60 or 80 grams per square meter. Examples of the outer layer of water vapor breathable material include Sympatex® brand water vapor permeable membranes made of polymers made by Sympatex Technologies, including monolithic hydrophilic polyester ester membrane, including, as one example, a 12 micron thick membrane. The outer tube 434 may include a more rigid material than the inner tube 432, to prevent the inner tube 432 from being damaged and/or punctured.

In some embodiments, the breathing circuit tubing 411 may, additionally or alternatively, include one or more small openings or perforations (not shown) in the inner tube 432 which permit drainage of liquid water from the breathing gas conduit 412 to the dry gas conduit 414. Therefore, a second moisture transmission pathway T1 may be provided by the one or more perforations between the breathing gas flow (B) and dry gas flow (D), as shown in FIG. 9. Although, the transmission pathway (T) and the second transmission pathway (T1) are depicted in the same cross-sectional view of FIG. 9, the transmission pathways (T, T1) may be provided in the alternative and/or at different portions along the breathing circuit tubing 11. The transmission pathway (T) and the second transmission pathway (T1) may be provided in a gradient along the length of the inner tube 432. For example, in some embodiments, the inner tube 432 may have more permeability at the upstream end 410A than the downstream end 410B, increasing moisture transfer when the breathing gas enters the breathing gas conduit 412 reducing condensation in remaining length of the inner tube 432. In some embodiments, the inner tube 432 may have more permeability on the downstream end 410B than the upstream end 410A, increasing moisture transfer when the moisture of the breathing gas is lower.

Figure 10:
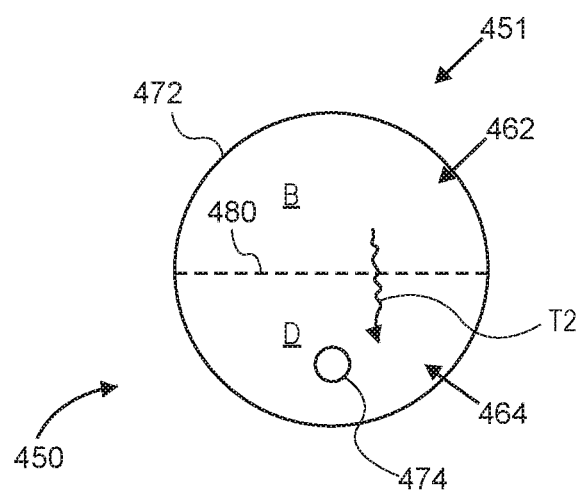
FIG. 10 is a schematic cross-sectional view illustrating the apparatus of FIG. 8 according to another implementation of the disclosure.

FIG. 10 is a schematic cross-sectional view illustrating the apparatus of FIG. 8 of one or more additional embodiments of the present disclosure. As depicted in FIG. 10, a breathing circuit tubing 451 may include a tube 472 including a breathing gas conduit 462 configured to receive a flow of breathing gas flow (B). The breathing gas may have a first humidity level and a first level of moisture. The tube 462 may also include a dry gas conduit 464 configured to receive a dry gas flow (D). The dry gas flow may have a second humidity level lower than the first humidity level, and/or a second level of moisture lower than the first level of moisture. The dry gas conduit 464 may be adjacent to at least a portion of the breathing gas conduit 462. A feeding conduit 474 may extend through the dry gas conduit 464. As further depicted in FIG. 10, a moisture transmission pathway (T2) may be provided between the breathing gas conduit 462 and the dry gas conduit 464, such that moisture and/or humidity may be transferred from the breathing gas (B) to the dry gas flow (D) based on the differential humidity/moisture levels. In the embodiment of FIG. 10, the breathing gas conduit 462 and dry gas conduit 464 may share a common dividing wall 480 providing the moisture transmission pathway (T2). For example, the moisture transmission pathway (T2) may be provided by a permeable portion or membrane (depicted as broken lines) incorporated into part or all of the dividing wall 480, as described herein, or a series of perforations in part or all of the dividing wall 480, as also described herein. The permeable portion may be permeable to water vapor but impermeable to liquid water and may include one or more layers, including a wicking layer, as described above.

In one or more embodiments of the present disclosure, the dry gas conduit 414, 464 may be closed to ambient air around the apparatus 410. The dry gas conduit 414, 464 therefore can be configured to provide a stream of dry gas flow at humidity levels which are significantly lower than the humidity in the breathing gas conduit 412, 462. In some embodiments, the apparatus 410 may include one or more sensors configured to detect the first humidity level of the breathing gas conduit 412 and the second humidity level of the dry gas conduit 414. The present disclosure therefore uses the differential between humidity or moisture content between the respective flows in the breathing gas conduit 412, 462, compared to the dry gas conduit 414, 464, which allows for greater extraction or diffusion of moisture and humidity from the breathing gas flow to the dry gas flow, which is further assisted by the convective action of the dry gas flow along the common surface area shared between the breathing gas conduit 412, 462, and the dry gas conduit 414, 464, such as along inner tube 432, or common dividing wall 480.

Figure 11:
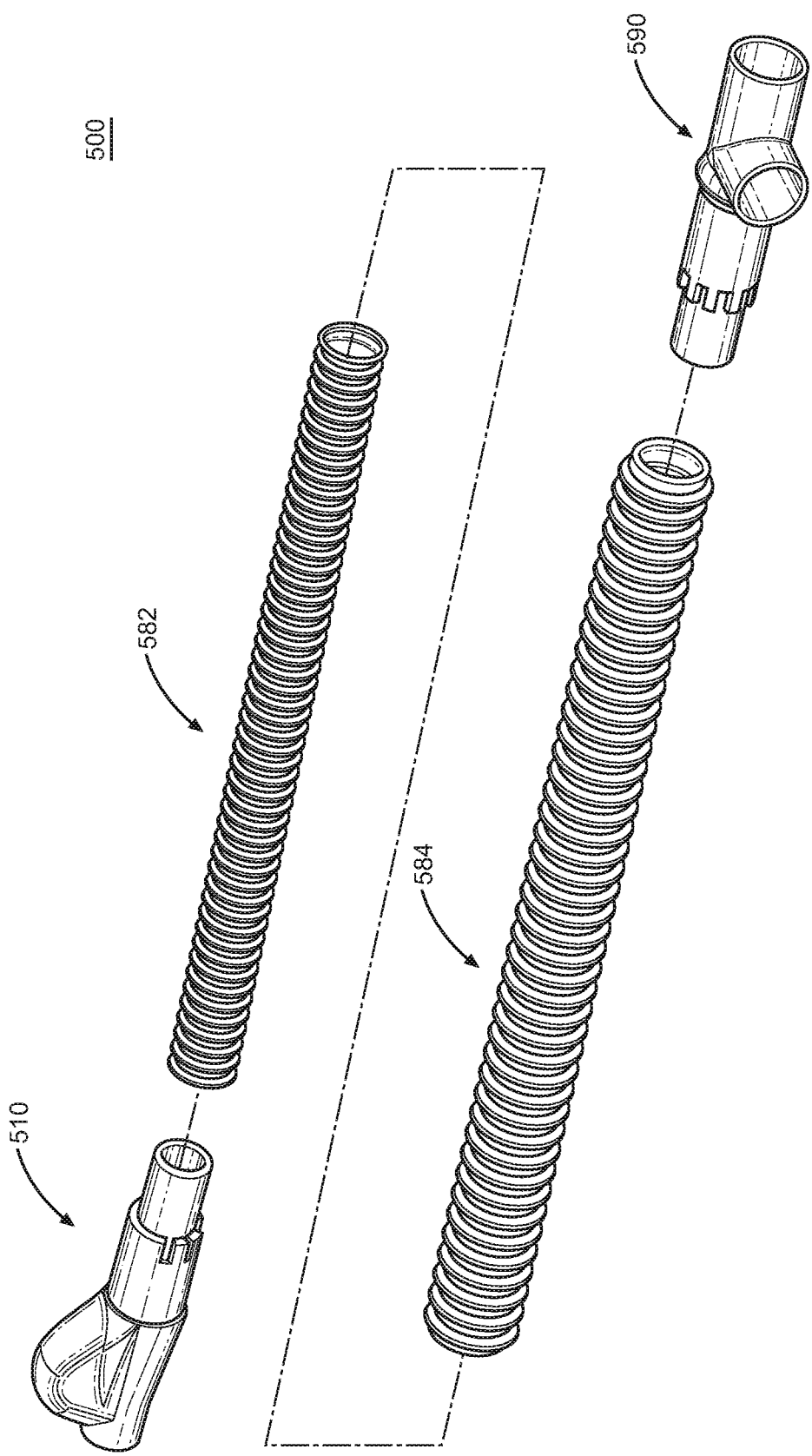
FIG. 11 is an exploded perspective view of a single-limb humidification system according to another implementation of the disclosure.
Figure 12:
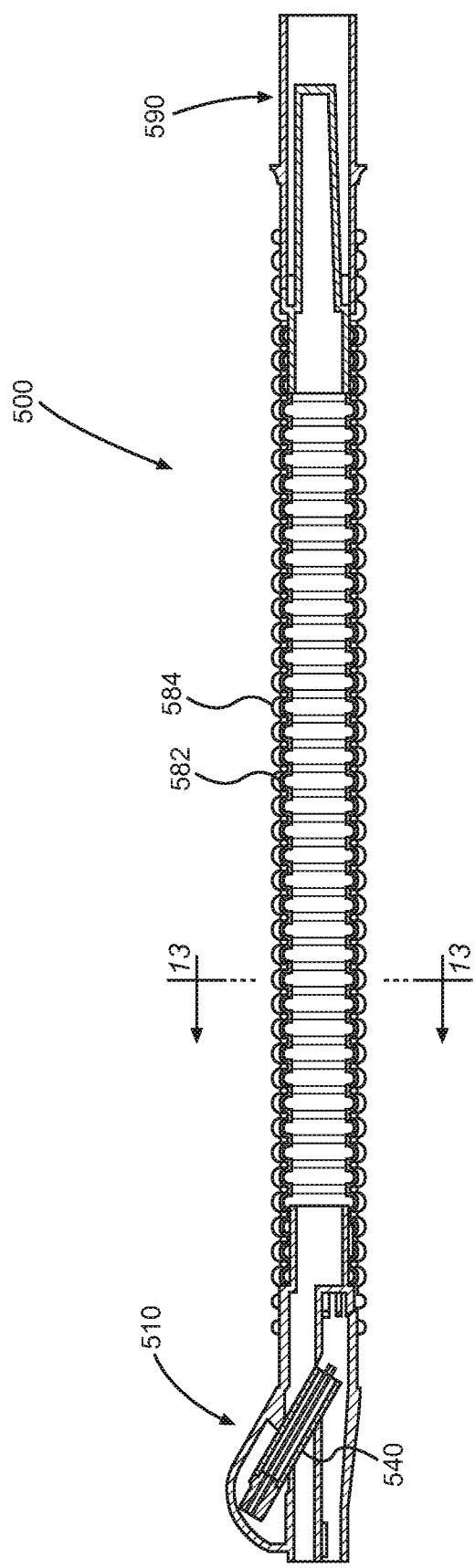
FIG. 12 is a side elevation cross-sectional view of the humidification system of FIG. 11.

Referring to FIGS. 11 and 12, an implementation of a single-limb respiratory humidification system 500 for on-demand near-patient humidification according to the present disclosure is shown. The single-limb respiratory humidification system 500 may comprise a humidification device according to another embodiment of the disclosure that is configured to add moisture to a breathing gas in order to adjust a humidity level thereof. The humidification device may include a patient coupling member 510, a vapor injection unit 540, an expiratory gas conduit 582, and an inspiratory gas conduit 584. The humidification system may also comprise a vent coupling member 590. The patient coupling member 510 is configured to couple the expiratory and inspiratory gas conduits 582, 584 to a patient or patient interface, such as an endotracheal tube, a breathing mask, or a nasal cannula, among others. In one aspect of the disclosure, the patient coupling member 510 may be provided at a location near the patient in order to avoid condensation buildup within the inspiratory gas conduit 584. The vent coupling member 590 is configured to couple the expiratory and inspiratory gas conduits 582, 584 to a ventilator and/or a flow meter to assist with supplying and/or circulating an airflow to the patient.

Figure 13:
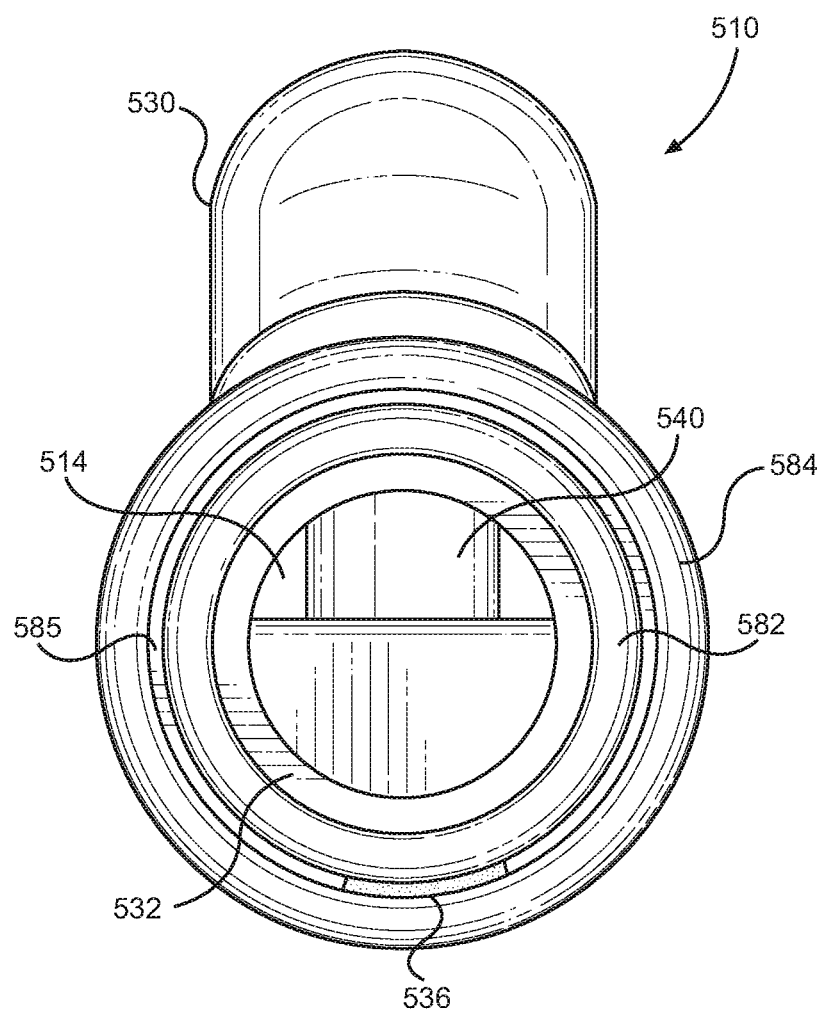
FIG. 13 is a front cross-sectional view of the system taken along line 13-13 of FIG. 12.

As illustrated in FIG. 13, the expiratory gas conduit 582 may be provided within the interior of the inspiratory gas conduit 584 to form a single limb breathing circuit in order to assist with humidification of the inspiratory gas flow, as will later be discussed in greater detail. In such a single limb arrangement, the expiratory gas conduit 582 defines an inner conduit and the inspiratory gas conduit 584 defines an outer conduit. Further, the expiratory and inspiratory gas conduits 582, 584 may be coaxially aligned so that expiratory gas is permitted to flow within the interior space of the expiratory gas conduit 582, and inspiratory gas is permitted to flow within the space 585 formed between the inspiratory gas conduit 584 and the expiratory gas conduit 582. More particularly, the expiratory and inspiratory gas conduits 582, 584 of the single limb implementation shown in FIGS. 11-13 may comprise cylindrically shaped flexible tubing that are concentrically arranged. Alternatively, it should be appreciated that the expiratory gas conduit 582 and the inspiratory gas conduit 584 may be non-concentrically aligned.

Figure 14:
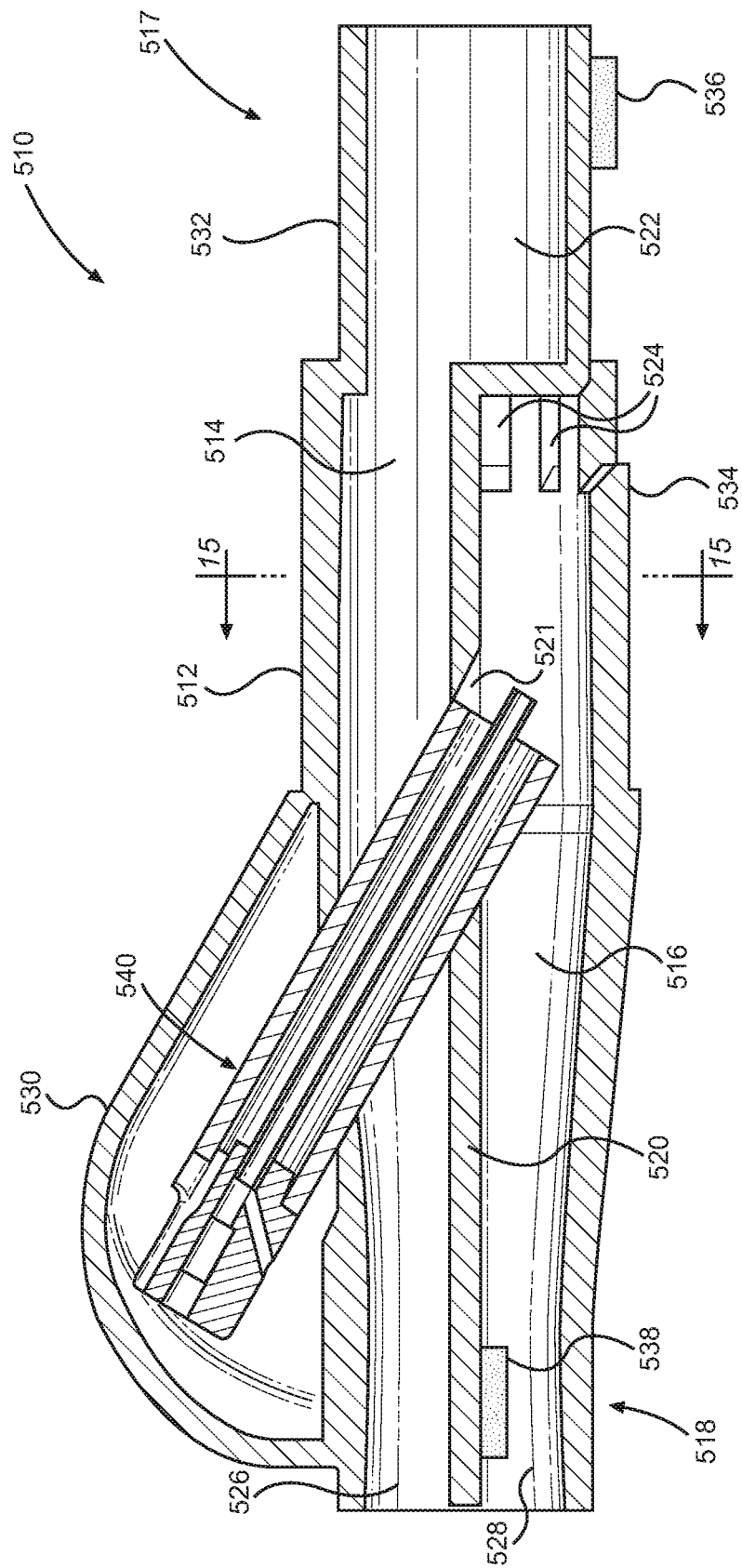
FIG. 14 is a side elevation cross-sectional view of a patient coupling member according the present disclosure.

Referring to FIG. 14, the patient coupling member 510 comprises a housing 512 defining an expiratory gas passage 514 in communication with the expiratory gas conduit 582, and an inspiratory gas passage 516 in communication with the inspiratory gas conduit 584. In particular, a proximal end 517 of the housing 512 may include an expiratory gas outlet 522 and at least one inspiratory gas inlet 524, and a distal end 518 of the housing 512 may include an expiratory gas inlet 526 and an inspiratory gas outlet 528. In one aspect of the disclosure, for example, three inspiratory gas inlets 524 may be provided to allow gas from the inspiratory gas conduit 584 to enter into the inspiratory gas passage 516 of the housing 512. Further, the proximal end 517 of the housing 512 may include an expiratory fitting portion 532 adapted to sealingly connect to an end of the expiratory gas conduit 582, and an inspiratory fitting portion 534 adapted to sealingly connect to an end of the inspiratory gas conduit 584. For example, the expiratory and inspiratory gas conduits 582, 584 may mate with the respective expiratory and inspiratory fitting portions 532, 534 of the patient coupling member 510 in a sealing manner, such as with a press-fit connection or a bonded connection using adhesive, in order to prevent leakage. The expiratory and inspiratory gas passages 514, 516 of the patient coupling member 510 may be separated by a barrier wall 520 so that expiratory gas and inspiratory gas do not mix within the housing 512.

According to another aspect of the disclosure, a vapor injection unit 540 may be disposed within the patient coupling member 510. The vapor injection unit 540 is configured to inject vapor into the inspiratory gas passage 516 of the patient coupling member 510, as will be discussed in greater detail below. The patient coupling member 510 may comprise a cap or cover 530. In one implementation, the vapor injection unit 540 may be disposed entirely within the housing 512. In another implementation, the vapor injection unit 540 may be at least partially disposed within the housing 512.

Figure 15:
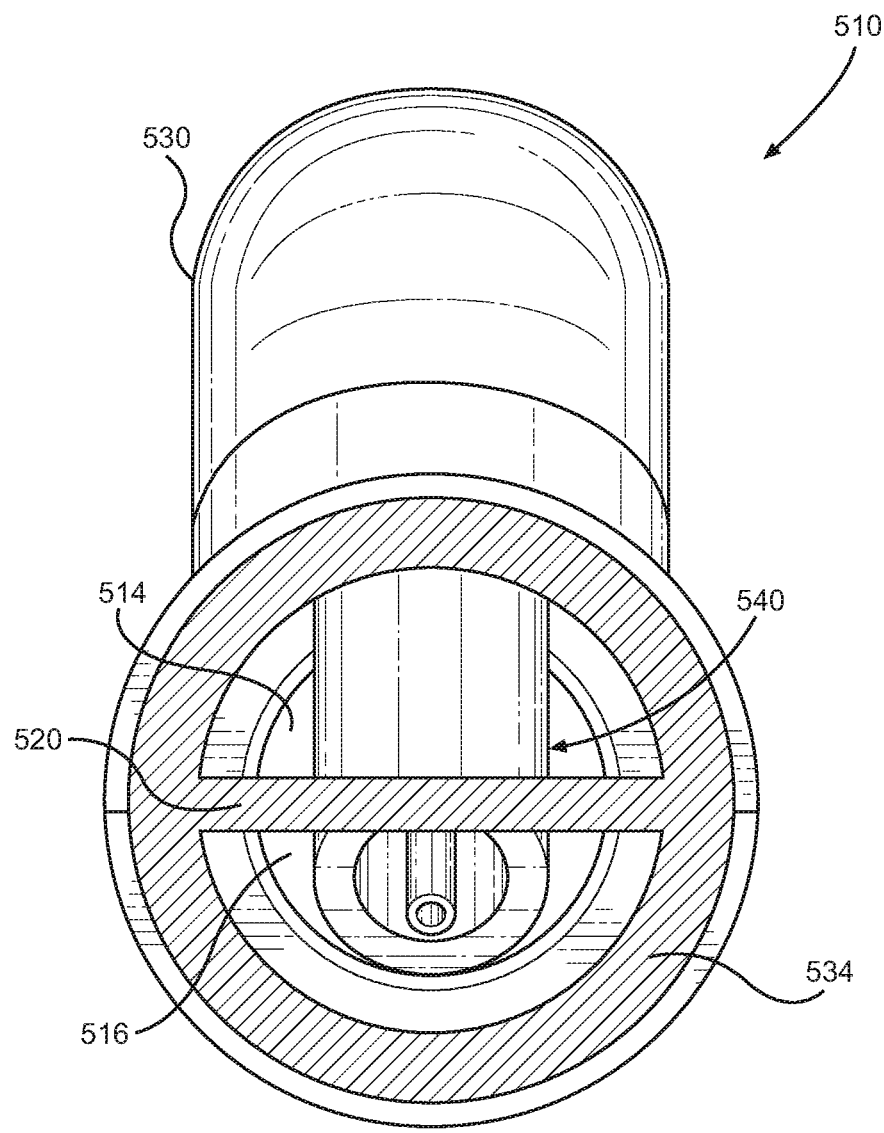
FIG. 15 is a front cross-sectional view of the system taken along line 15-15 of FIG. 14.

In the implementation shown in FIGS. 14 and 15, the cap or cover 530 is located directly adjacent to the expiratory air passage 514, and the vapor injection unit 540 is disposed within both the expiratory and inspiratory gas passages 514, 516. An access hole 521 provided in the barrier wall 520 of the patient coupling member 510 permits the vapor injection unit 540 to pass through the barrier wall 520 such that a dispensing end of the vapor injection unit 540 is in fluid communication with only the inspiratory gas passage 516. This arrangement provides a compact design of the patient coupling member 510 allowing for unobtrusive placement near a patient. In one aspect, the vapor injection unit 540 may be oriented along an axis forming an acute angle to the central axis of the inspiratory gas conduit 584.

When the vapor injection unit 540 passes through the expiratory gas passage 514, expiratory air is permitted to flow around the exterior of the vapor injection unit 540. Thus, the vapor injection unit 540 injects vapor directly into the inspiratory gas passage 516 of the patient coupling member 510 to mix with the inspiratory gas flow. This arrangement ensures that only the inspiratory gas passage 516 receives vapor dispensed from the vapor injection unit 540. Further, the vapor injection unit 540 may form a tight sealing fit with the access hole 521 in the barrier wall 520 of the patient coupling member 510 in order to prevent gas seepage between the expiratory and inspiratory gas passages 514, 516. In other aspects, a sealing member such as an O-ring may be provided between the vapor injection unit 540 and the access hole 521 to prevent gas seepage. In another implementation, the cap or cover 530 may be located directly adjacent to the inspiratory air passage, and the vapor injection unit 540 may be disposed within the inspiratory gas passage 516 of the patient coupling member 510 but not within the expiratory gas passage 514. In some implementations, the vapor injection unit 540 and the patient coupling member 510 may be separate components of a humidification device, such that the vapor injection unit 540 is removably received within the patient coupling member 510 so that it can be replaced. In other implementations, the vapor injection unit 540 and the patient coupling member 510 may be combined to form a single integral humidification device.

Figure 16:
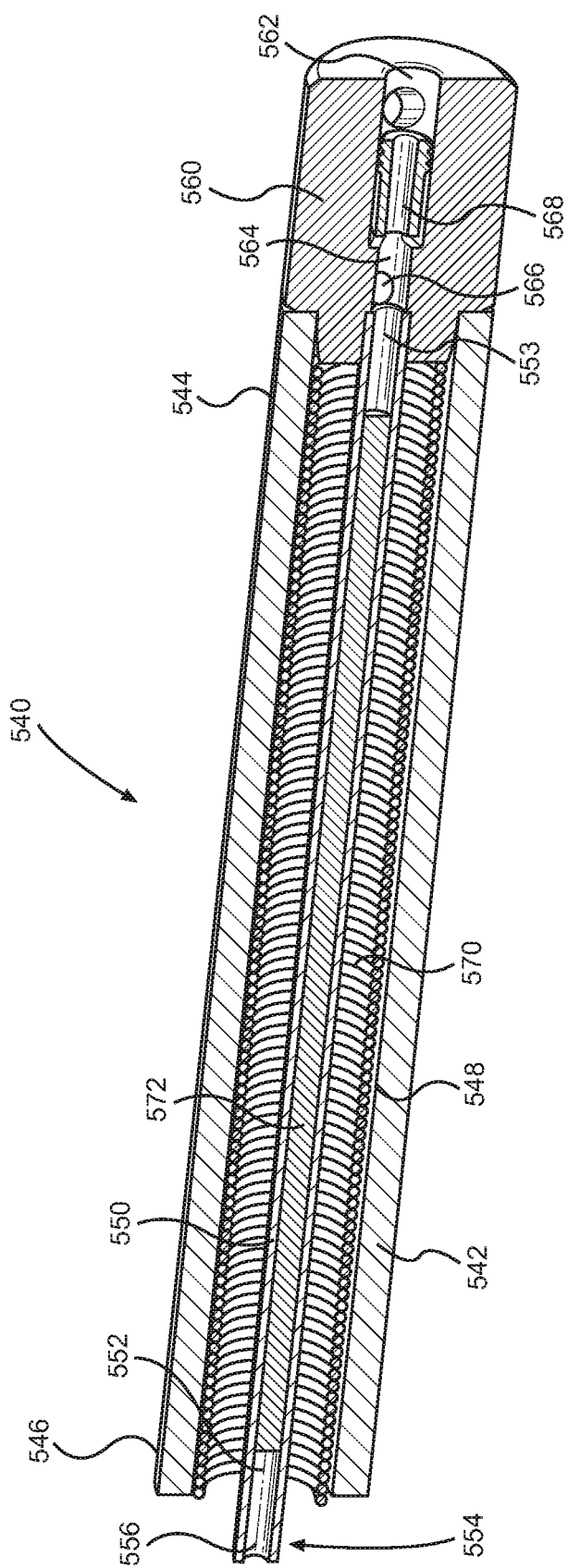
FIG. 16 is a perspective side cross-sectional view of a vapor injection unit according to the present disclosure.

The vapor injection unit 540 is configured to heat fluid, such as water, and transform it into vapor, such as steam. The vapor injection unit 540 is further configured to inject the steam into the inspiratory gas passage 516 of the patient coupling member 510 in order to provide humidity to a dry inspiratory air flow for a patient to breathe in. As illustrated in FIG. 16, the vapor injection unit 540 comprises a hollow injection housing or vapor housing 542 that includes a proximal end 544, an opposite distal end 546, and an inner injection housing lumen 548 extending from the proximal end 544 of the injection housing 542 to the distal end 546 of the injection housing 542. The injection housing 542 may have an elongated tubular shape.

In one aspect, the injection housing 542 may be a thermal insulator comprising ceramic or other thermally insulating material. For example, the injection housing 542 may comprise material having low thermal conductivity in order to reduce heat transfer through a wall of the injection housing 542 and into the gas flow. The thermal insulator may include ceramics, glass, composite materials such as glass-bonded mica (Mykroy/Mycalex), fiberglass, insulating plastics, or other suitable materials having low thermal conductively. The injection housing 542 may be formed from extruded tubing or another suitable process, such as an injection molding process.

A cannula 550 may be disposed within the injection housing 542 and includes an inner cannula lumen 552 configured to receive a fluid. The cannula 550 may have a fluid supply end 553 configured to receive fluid, such as water, and a vapor dispensing end 554 defining a vapor outlet configured to dispense vapor. The inner lumen 552 of the cannula 550 extends from the fluid supply end 553 to the vapor dispensing end 554. In one implementation, the vapor dispensing end 554 of the cannula 550 may have a longitudinal length extending beyond the distal end 546 of the injection housing 542 and further defines a vapor outlet 556. The cannula 550 may be made from materials such as stainless steel, glass, ceramic, or other suitable materials. The cannula 550 may be magnetic or non-magnetic. In one aspect, the cannula 550 may comprise material having low thermal conductivity.

A hub 560 may be connected to the proximal end 544 of the injection housing 542 and is configured to connect to a fluid supply source, such as a water reservoir. The hub 560 may comprise a fluid inlet 562 for receiving fluid from the fluid supply source, and a fluid channel 564 having a check valve 568 disposed therein. The check valve 568 may be a one-way valve configured to prevent backflow of fluid through the fluid channel 564. The check valve 568 may be implemented with at least one of a ball check valve, a diaphragm check valve, a swing check valve, a stop-check valve, a pneumatic non-return valve, or another similar mechanical valve. The check valve 568 may close the supply of water entering the cannula 550 as a result of steam pressure formed within the inner cannula lumen 552.

The hub 560 may be connected to the fluid supply end 553 of the cannula 550 such that the fluid channel 564 is in fluid communication with the inner lumen 552 of the cannula 550. The injection housing 542 and the cannula 550 may each have a tubular shape and be concentrically arranged. In one implementation, the hub 560 may be formed around the fluid supply end 553 of the cannula 550 in an overlapping manner. The hub 560 may have a standardized Luer connection or a custom connection configured to releasably connect to the fluid supply.

A heater element 570, such as an induction element, may be disposed within the inner injection housing lumen 548 of the injection housing 542 and span along a length of the injection housing 542 from the proximal end 544 to the distal end 546. In one aspect, the induction element 570 may surround at least a portion of the cannula 550. In another aspect, the induction element 570 may wrap around and contact the exterior of the cannula 550. Further, a heating element 572 may be provided within the inner lumen of the cannula 550, and arranged therein such that a space is provided between the heating element 572 and the inner wall of the cannula lumen 552 to permit a flow of fluid to pass therethrough in order to be heated and transformed into vapor. The induction element 570 may be an induction coil formed from a single or multiple enameled wires. In one implementation in which the induction element 570 is formed from multiple wires, the multiple wires may be twisted to form a Litz wire in order to reduce power loss and heat generated by the "skin effect" at high alternating current (AC) frequencies. It should further be appreciated that the induction element may comprise a rectangular cross-section magnet wire which provides similar results as the aforementioned Litz wire. Further, according to another aspect, power to the induction element 570 may be switched to ground, or between positive and negative voltages. The voltage waveform may be square for providing most efficiency, sinusoidal for minimizing EMI, or another waveform such as triangular or sawtooth. The induction element 570 may be center-tapped, and a positive voltage may be supplied at the center tap. The ends of the induction element 570 may be alternately switched to ground to generate an oscillating magnetic field within the interior of the induction element 570. The oscillating magnetic field created from the induction element 570 may produce eddy currents in order to heat the heating element 572 located within the cannula 550. In other implementations of the disclosure, the heater element 570 may be a conduction element, and the heating element 572 may be a conduction heating element configured to be heated by conduction.

In other aspects, the heater element 570 may be a pair of parallel electrical conductors configured to generate a dipole. The pair of parallel electrical conductors may be provided within the injection housing inner lumen and extend parallel to its central axis. The pair of parallel electrical conductors may be insulated wires or conductive tracks formed onto a flexible printed circuit. A positive voltage may be supplied to one of the electrical conductors in order to generate a dipole. The two ends of the other electrical conductor may be alternately switched to ground at a high frequency in order to generate an oscillating magnetic field within the injection housing lumen 548.

In further aspects, the heater element 570 may be more than two pairs of electrical conductors configured to generate an oscillating magnetic field having multiple poles, such as a quadrupole, hexapole, octupole, or another multipole system with either an even or odd number of magnetic poles. The pairs of electrical conductors may similarly extend within the injection housing lumen along its central axis. The electrical conductors may be insulated wires or conductive tracks formed onto a flexible printed circuit board. A positive voltage may be supplied to one set of electrical conductors. The set of electrical conductors may be alternately switched to ground at a high frequency to create a rapidly oscillating magnetic field. In other aspects, a circuit may be used to switch the polarity of each end of the induction element 570 to improve efficiency of the induction element 570.

The induction element 570 may generate an oscillating magnetic field with frequencies up to 200 kHz. In further aspects, electromagnetic shielding, specifically radio frequency shielding, may be necessary such that the heater assembly 100 meets various regulatory electro-magnetic emission requirements.

The vapor injection unit 540 may further include a power and controls interface assembly (not shown) connected to the injection housing 542 and/or the hub 560. The power and controls interface assembly is configured to provide electrical power and control to the induction element 570 for heating the heating element 572. In one implementation, the power and controls interface assembly may be integral with the vapor injection unit 540 to form a single component. In another implementation, the power and controls interface assembly may be a connector receptacle or other interface adapted to facilitate a quick connection and/or disconnection with an electrical power source and/or control module. In another implementation, the power and controls interface assembly may include an electrical power source and be removably coupled to the vapor injection unit 540.

The vapor injection unit 540 may also include a thermocouple configured to measure temperature. The thermocouple may allow a user to monitor and/or provide closed-loop temperature control of the heating element. The thermocouple may be integrated with the heating element as a single component. In other aspects, the thermocouple may be a separate component from the heating element. For example, the thermocouple may be integrated into the cannula 550 and/or be placed in contact with the fluid path, which may allow the cannula 550 and/or fluid to act as a conductor, such that at least a portion of the measured thermocouple voltage is measured across the cannula 550 and/or fluid. In another implementation, the thermocouple may comprise a wire having electrical contacts (not shown) connected with the power and controls interface assembly. The electrical connection may be established using insulated wires and/or flexible printed circuits. An access opening 566 may be provided in the hub for passage of wires. It should be appreciated that the vapor injection unit 540 may use other devices, such as thermistors or resistance temperature detectors (RTDs), to measure temperature. The power and controls interface assembly may provide electrical power to the induction element 570 and/or thermocouple electrical contacts.

The thermocouple may be made from a magnetic material, such as Mu-metal, Alumel, iron, nickel, permalloy, or another alloy, to allow the thermocouple to interact with the oscillating magnetic field generated by the induction element 570 in order to produce heat, thus increasing the efficiency of the heating element. In some implementations, the thermocouple may be made from the same material as the heating element 572 to simplify construction. In other aspects, the thermocouple may be made from a non-magnetic alloy, or an alloy having low thermal conductivity, in order to reduce generation of induction heating and improve accuracy of the temperature measurements. Non-magnetic materials may include copper, Nicrosil, Nisil, Chromel, Constantan, or other similar alloys.

The heating element 572 located within the cannula 550 may be made from a magnetic material such as Mu-metal, Alumel, nickel, iron, permalloy, or other materials with a high relative magnetic permeability. The heating element 572 may be a tube, a solid cylinder such as a rod or wire, a matrix of cylinders, a sintered cylinder, a porous cylinder, a sheet, a spiral sheet, a coil, or any combination thereof. For instance, the heating element 572 may be a twisted or helical coil of wires. The heating element 572 may extend along the entire length of the cannula 550 or along a portion of the cannula. The heating element 572 may be configured to interact with the oscillating magnetic field generated by the induction element 570. The heating element 572 can have a high magnetic permeability because the efficiency of induction heating within the heating element 572 may be greater.

Figure 17:
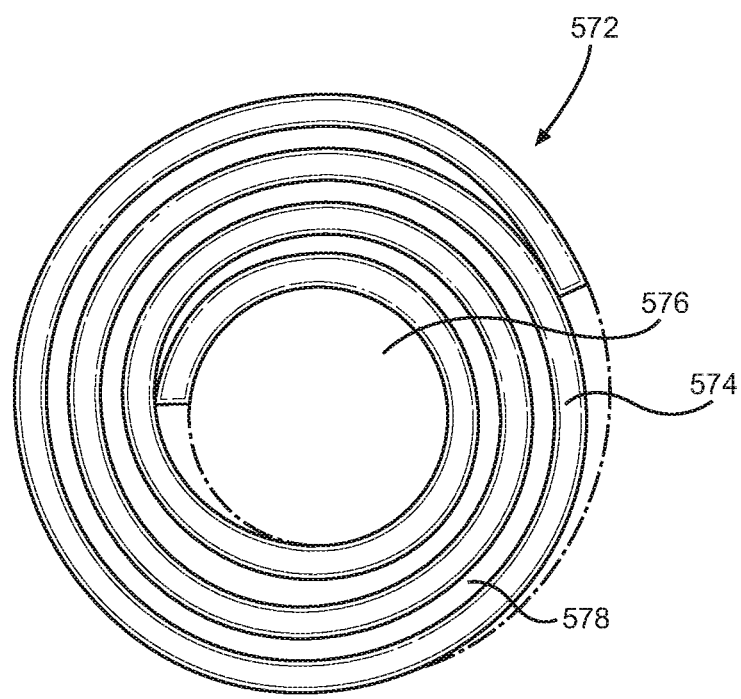
FIG. 17 is a front cross-sectional view of a heating element according to the present disclosure.

In one implementation, the shape of the heating element 572 core may match the shape of the inner cannula lumen 552. In another implementation, the heating element 572 may comprise a rolled foil having a jelly roll shape, as illustrated in FIG. 17. The rolled foil heating element 572 comprises a foil 574 that may be spirally wrapped around a wire or rod mandrel core 576. In another implementation, it should be appreciated that the heating element may include the spirally rolled foil 574 but not the mandrel core 576. For instance, the mandrel core may be optional in order to provide an easier assembly. Further, magnetic fields at the frequencies described herein may induce heat only within about three to four outer layers of the spiral wrapped foil. In other implementations, the mandrel core 576 may be an axial array of magnetic material in the form of wires, rods, plates, or tubes. In some aspects, integration of the mandrel and foil may be in the form of knurled, drawn or extruded radial flats, grooves, fins or other features, as well as helical modification thereof. Both the mandrel core 576 and the foil 574 may comprise a magnetic material as previously described, such as Mu-metal, Alumel, nickel, iron, permalloy, or other materials with a high relative magnetic permeability.

A gap 578 formed between adjacent layers of wrapped foil 574 provides a tortuous pathway for water to travel therethrough. Such a rolled foil heating element 572 permits increased heat transfer to fluid water with minimal restriction to flow through and around the induction heating element 572. Thus, the rolled foil heating element 572 can have a greater surface area for contacting fluid to increase the efficiency of heat transfer between the fluid pumped into the cannula 550 and the heating element 572.

In one aspect of the rolled foil heating element 572 shown in FIG. 17, a Mu-metal foil may have a thickness of approximately 0.002 inches or less, and produce higher heat generation for a given induction frequency when compared with other selected magnetic materials and thickness. In another aspect, the mandrel core 576 may produce a higher heat generation for a given induction frequency when compared with other known materials (magnetic and non-magnetic). In another aspect, a maximum heat transfer to fluid may occur when a gap of 0.002 inches or less is provided between adjacent layers of the wrapped foil 574 over a total length of four inches or less. In another aspect, a gap of 0.0005 inches (approximately 12 microns) or greater between layers of the wrapped foil 574 over a length of one or more inches may ensure that the fluid remains in contact with the heating element 572 for a duration of time sufficient to transfer energy (in the form of heat) to water in order to ensure complete transformation of room temperature water into gas, such as steam. Such evaporation/vaporization of water may be maximized when the outer diameter of the heating element 572 (i.e., the combination of the foil 574 and mandrel core 576) is 0.5 inches or less. Moreover, in other aspects, the mandrel core 576 may have a circular cross-section in order to produce optimal heating effects for a given length when compared to a mandrel core having a square, pentagonal, hexagonal, or other geometrically shaped cross-section. In other implementations, the rolled foil heating element 572 may increase electrical inductance by approximately 50% when used in conjunction with rectangular magnet windings having an approximate 4:1 width to thickness ratio, thus indicating increased performance.

Figure 18:
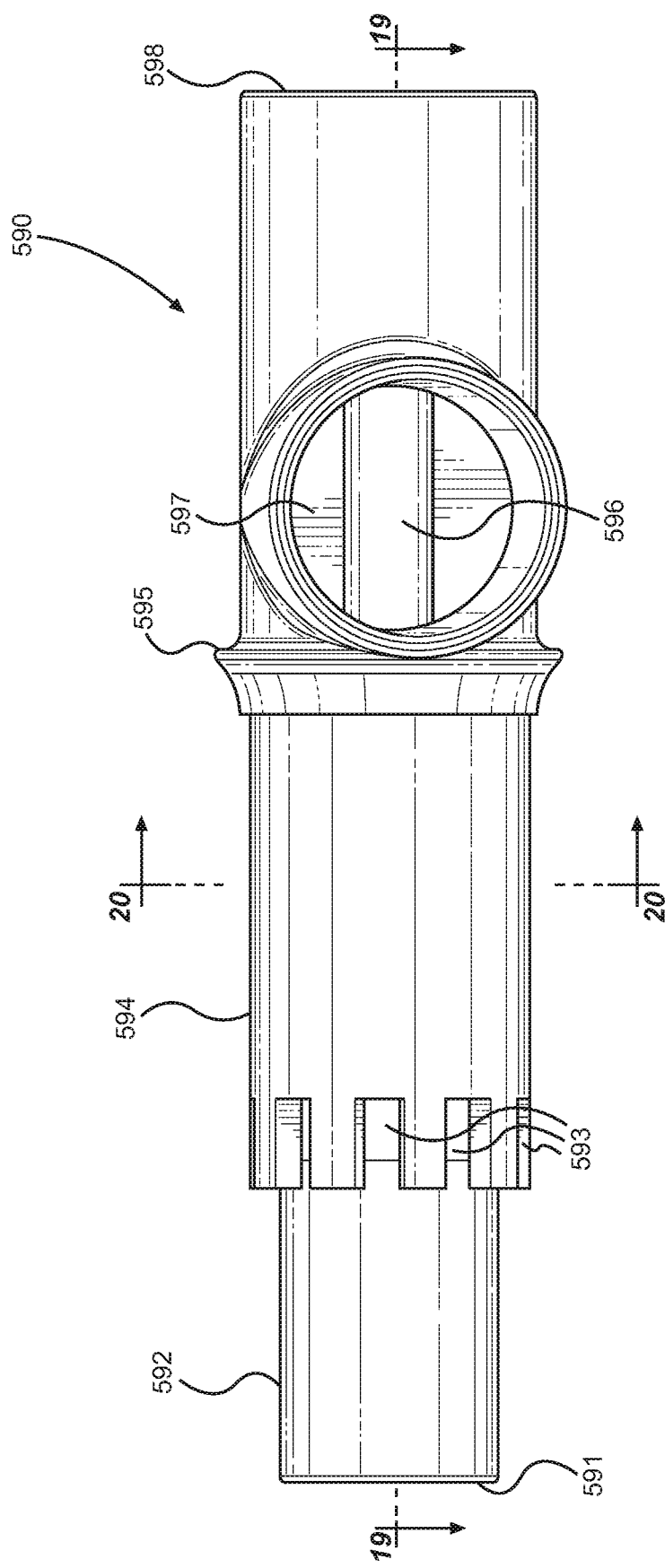
FIG. 18 is a side elevation view of a vent coupling member according to the present disclosure.
Figure 19:
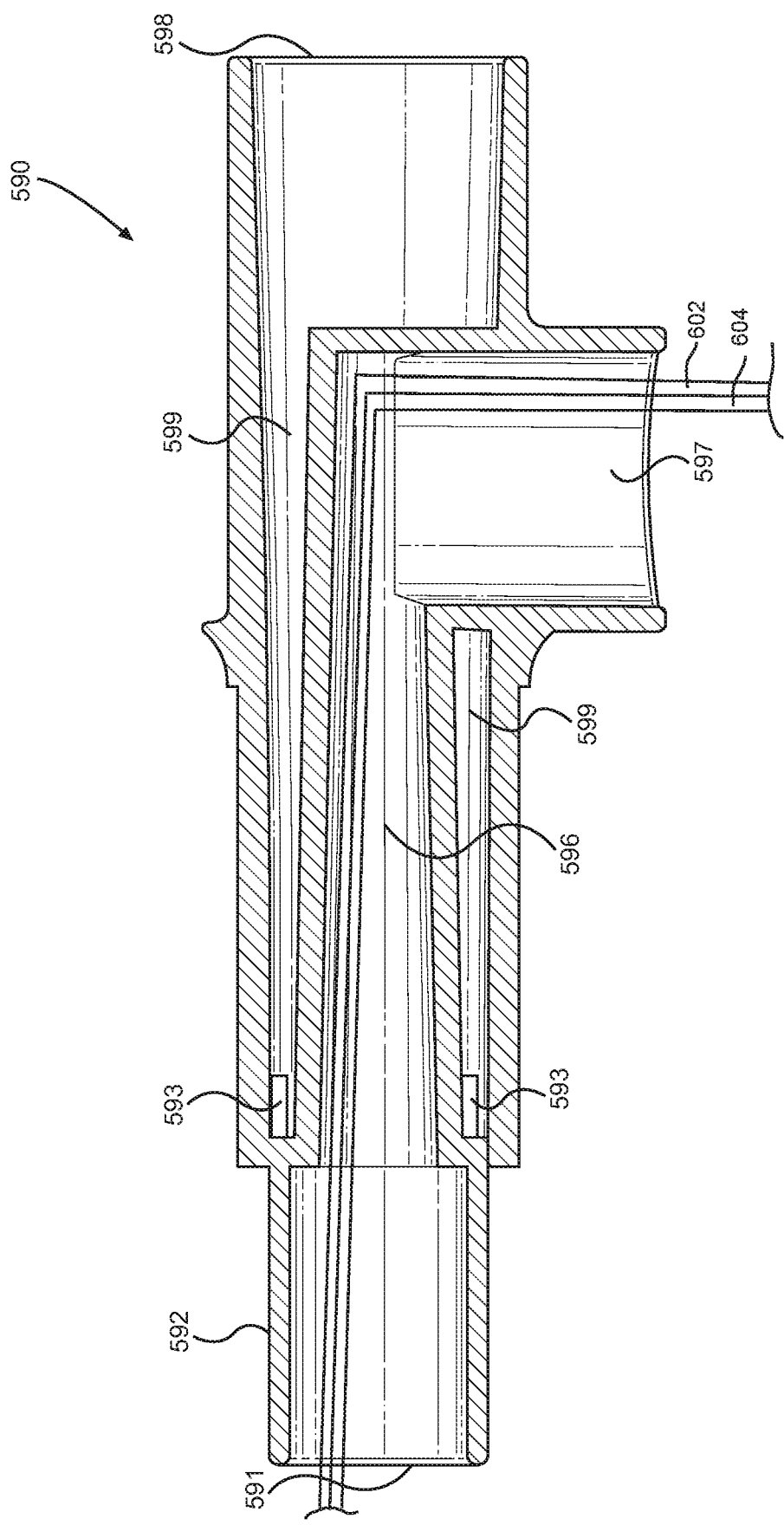
FIG. 19 is a top cross-sectional view of the vent coupling member taken along line 19-19 of FIG. 18.
Figure 20:
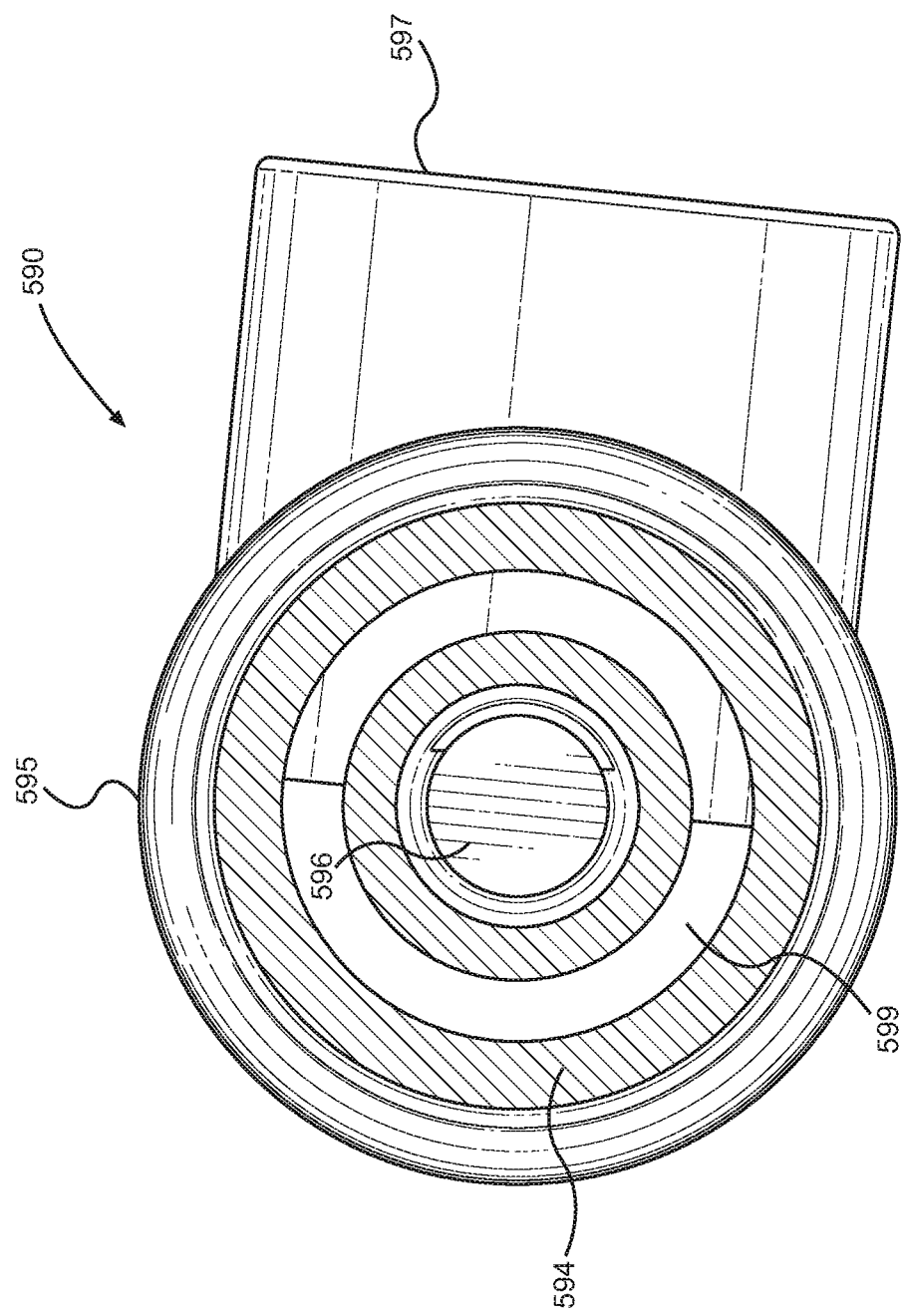
FIG. 20 is a front cross-sectional view of the vent coupling member taken along line 20-20 of FIG. 18.

Referring to FIGS. 18-20, the vent coupling member 590 is configured to couple the expiratory and inspiratory gas conduits 582, 584 to a ventilator and/or a flow meter to assist with supplying and/or circulating a flow of gas to the patient, as previously described above. The vent coupling member 590 comprises an expiratory gas inlet 591 and an expiratory fitting portion 592 adapted to sealingly connect to an end of the expiratory gas conduit 582. The vent coupling member 590 further comprises at least one inspiratory gas outlet 593 and an inspiratory fitting portion 594 adapted to sealingly connect to an end of the inspiratory gas conduit 584. The expiratory and inspiratory gas conduits 582, 584 may be adapted to mate with the respective expiratory and inspiratory fitting portions 592, 594 of the vent coupling member 590 in a sealing manner, such as with a press-fit connection or a bonded connection using adhesive, in order to prevent leakage. An annular lip 595 may be provided adjacent to the inspiratory fitting portion 594 for a user to grip when connecting or disconnecting the vent coupling member 590 from the gas conduits, vent, and/or flow meter.

Expiratory gas that enters the vent coupling member 590 through the expiratory gas inlet 591 travels through an expiratory gas channel 596 and exits through an expiratory gas outlet to the ventilator. Further, dry inspiratory gas supplied from the ventilator enters into the vent coupling member 590 through an inspiratory gas inlet 598. The inspiratory gas travels through an inspiratory gas channel 599 and exits through the at least one inspiratory gas outlet 593 into the inspiratory gas conduit 584 of the breathing circuit. In one implementation, the expiratory and inspiratory gas channels 596, 599 are separated by a dividing wall so that expiratory and inspiratory gas does not mix. In one aspect, the expiratory and inspiratory gas channels may be further concentrically aligned. In another aspect, the inspiratory gas inlet 598 and the expiratory gas outlet 597 may be aligned perpendicular to each other. Similarly, expiratory gas inlet 591 and the expiratory gas outlet 597 may be perpendicularly aligned. The dry inspiratory gas may then flow within the inspiratory gas conduit 584 toward the patient. The inspiratory gas may enter the at least one inspiratory gas inlet 524 of the patient coupling member 510. The dry inspiratory gas may accumulate moisture transferred from the expiratory gas conduit 582, as will be discussed in greater detail below. In another aspect, an electrical power/signal cable 602 and/or fluid supply lumen 604 may be provided in the breathing circuit. For instance, the power/signal cable 602 and the fluid supply lumen 604 may extend through the vent coupling member 590, one of the breathing gas conduits, and the patient coupling member 510 in order to be electrically and fluidly connected, respectively, to the vapor injection unit. In some aspects, the power/signal cable 602 and/or fluid supply lumen 604 may be provided within the expiratory gas conduit 582 or the inspiratory gas conduit 584.

A first or pre-heater sensor 536 may be located at the proximal end 517 of the patient coupling member 510 at an upstream location of the inspiratory gas flow relative to the vapor injection location. In one implementation, the first or pre-heater sensor 536 may be connected to an outer surface of the expiratory fitting portion 532 of the patient coupling member 510 as shown in FIG. 14. The first or pre-heater sensor 536 may be configured to measure a first temperature and a first humidity of the inspiratory gas flow prior to the introduction of vapor from the vapor injection unit 540. A second or post-heater sensor 538 may be located at the distal end 518 of the patient coupling member 510 at a downstream location of the inspiratory gas flow relative to the vapor injection location. The second or post-heater sensor 538 may be connected to an inner surface of the inspiratory gas passage 516 of the patient coupling member 510 as shown in FIG. 14. The second or post-heater sensor 538 may be configured to measure a second temperature and a second humidity of the inspiratory gas flow after vapor has been dispensed into the inspiratory gas flow from the vapor injection unit 540. Further, the first and second sensors 536, 538 may each be configured to separately measure temperature and humidity independently. In some aspects, the first and second sensors may be spaced equally apart from the vapor injection location. Further, it should be appreciated that the both the first and second sensors 536, 538 may comprise a flexible circuit in communication with the power and control interface.

A controller in communication with the vapor injection unit 540 via a connection with the power and control interface may be configured to control an amount of vapor injected into the inspiratory gas passage 516 for mixing with the inspiratory gas that enters the patient coupling member 510. The injected vapor may have a vapor temperature determined as a function of the measured first and second temperatures and the measured first and second humidities of the inspiratory breathing gas.

Figure 21:
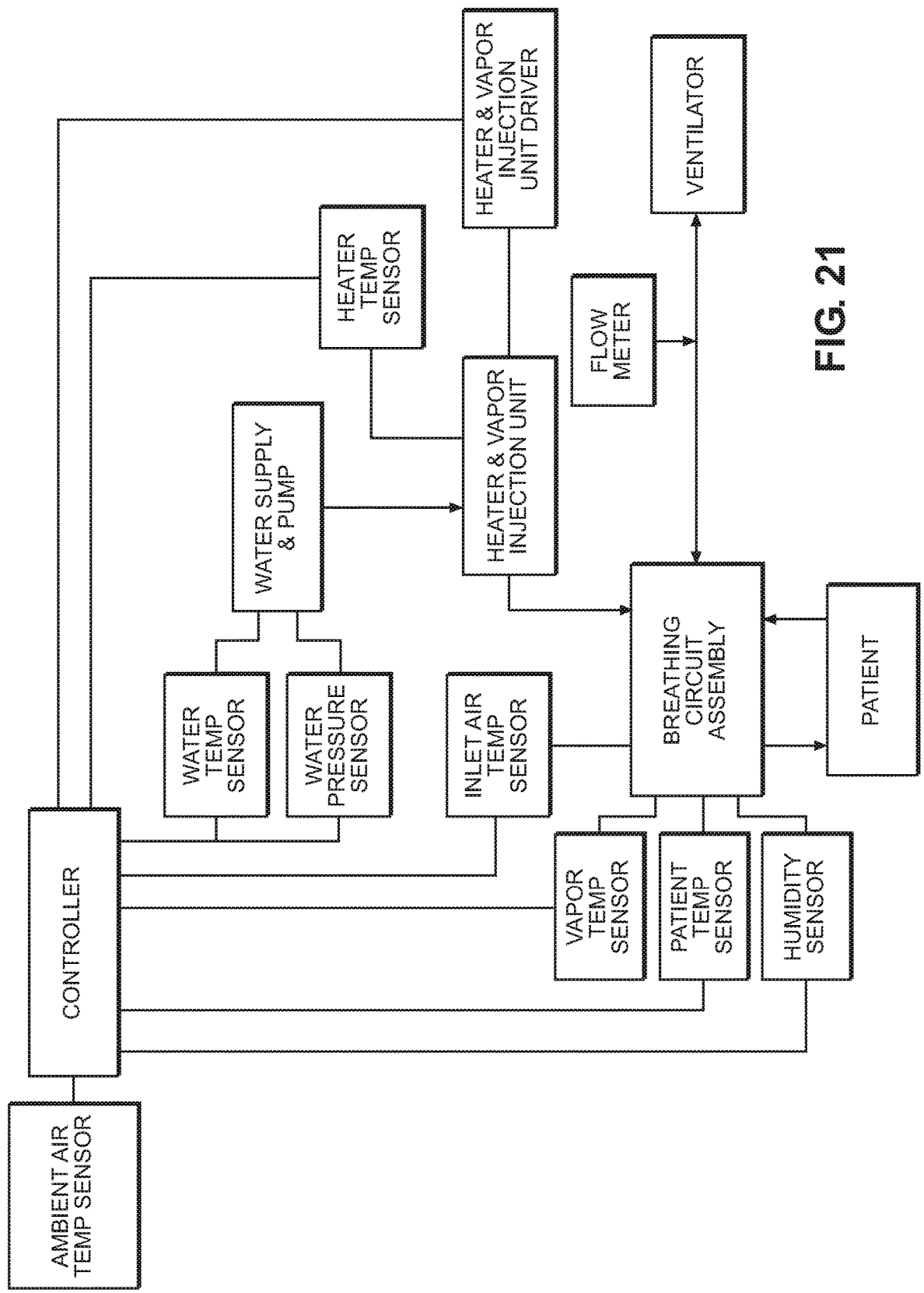
FIG. 21 is a schematic diagram of the humidification system according to an implementation of the disclosure.

FIG. 21 illustrates a schematic representation of an implementation of a process for simultaneously and independently controlling the temperature and humidity of inspiratory gas in a respiratory breathing circuit using the near-patient humidification system described herein. As shown, the process comprises supplying a breathing gas to the respiratory breathing circuit; measuring a first temperature and a first humidity of the breathing gas at a location upstream from a vapor injection unit; measuring a second temperature and a second humidity of the breathing gas at a location downstream from a vapor injection unit; and injecting vapor from the vapor injection unit into the respiratory breathing circuit assembly, the vapor having a vapor temperature determined as a function of the measured first and second temperatures and the measured first and second humidities of the breathing gas. In some aspects, data provided by the flow meter may be provided by the ventilator.

Referring again to FIG. 16, for operation of the vapor injection unit 540, the induction element 570 may be excited to generate an oscillating magnetic field in order to create eddy currents within the heating element 572. The eddy currents generated in the heating element 572 may heat the heating element 572 to a desired temperature. Water may be pumped into the fluid inlet of the hub 560 and past the one-way valve in order to enter the fluid supply end 553 of the cannula 550. Water passes the heating element 572 as it travels through the cannula 550 and rapidly absorbs heat, thus vaporizing the water into steam. The rapid expansion of steam as it forms during vaporization may cause pressurized steam to be dispensed from the vapor outlet of the cannula 550 and injected into the inspiratory gas passage 516 of the patient coupling member 510 in order to humidify the inspiratory gas flow. It should be appreciated that the process may repeat in a cyclical fashion resulting in steam periodically being injected into the patient's breathing circuit to humidify the inspiratory breathing gas.

The humidified breathing gas then exits the inspiratory gas outlet of the patient coupling member 510 and is directed to a patient interface, such as an endotracheal tube or a breathing mask, for delivery to the patient. Expiratory gas that is expelled from the patient enters into the patient coupling member 510 via the expiratory gas inlet 526, travels through the expiratory gas passage 514, and exits from the expiratory gas outlet 522 directly into the expiratory gas conduit 582. The expiratory gas may travel back toward the vent coupling member 590, where it enters into the expiratory gas inlet 591, passes through the expiratory gas channel 596, and thereafter exits from the expiratory gas outlet 597 and into the ventilator.

Figure 22:
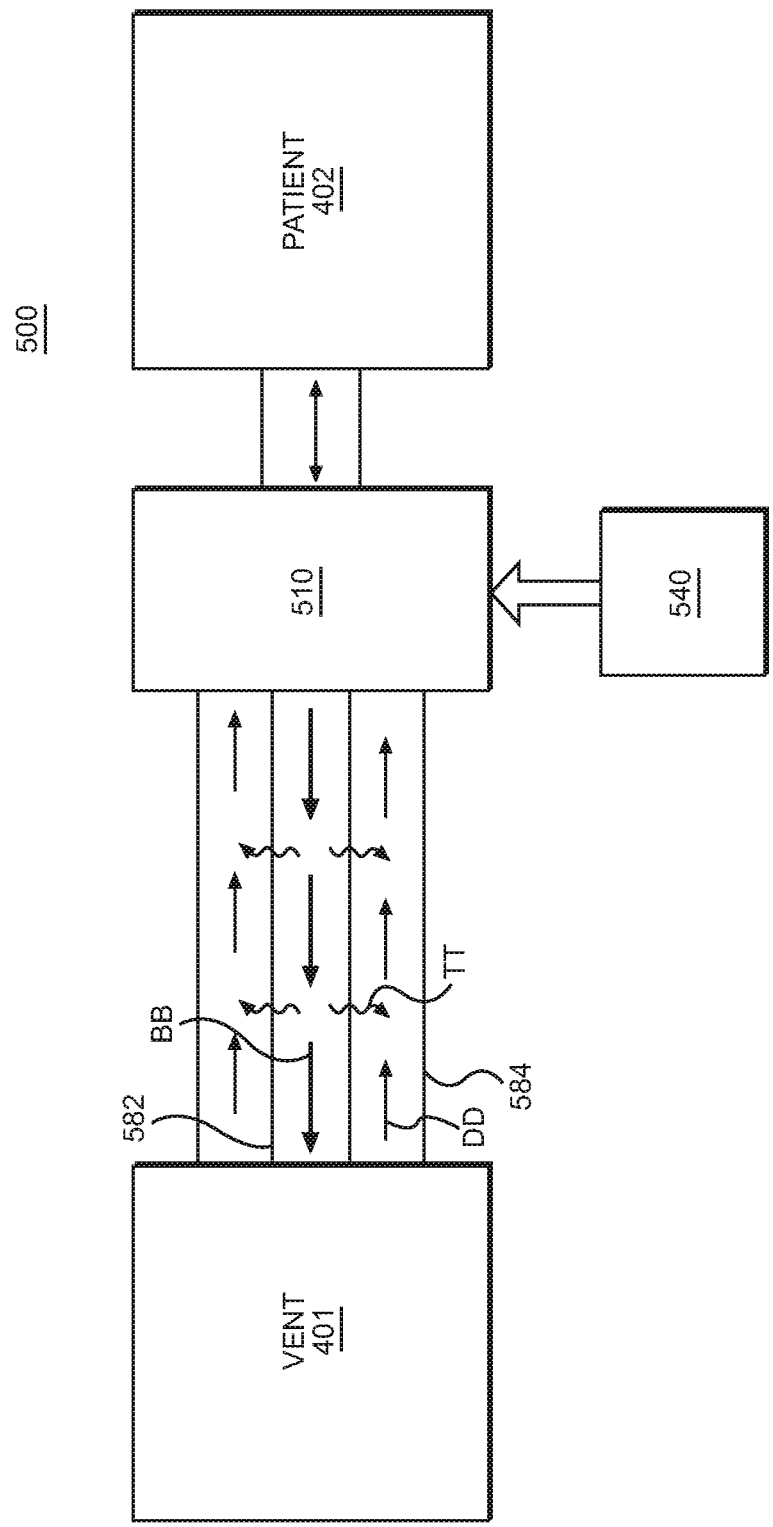
FIG. 22 is a schematic diagram of a single-limb humidification system according to another implementation of the disclosure.

As further shown in the schematic diagram of FIG. 22, the single-limb implementation of the humidification system according to the present disclosure is configured to provide a moisture transmission pathway between the expiratory gas conduit 582 and the inspiratory gas conduit 584, thus lowering the moisture and/or humidity in the flow of breathing gas (BB) expelled from the patient by transferring the moisture and/or humidity to a dry inspiratory gas flow (DD) provided to the patient. For example, the moisture transmission pathway (TT) may occur between the higher humidity breathing gases in the expiratory gas conduit 582 and the lower humidity dry gas flow in the inspiratory gas conduit 584. The moisture level thus may be reduced from within the expiratory breathing gas flow (BB) and transferred to the inspiratory dry gas flow (DD).

In some embodiments, the expiratory conduit 582 may include a permeable portion or membrane along its entire length or a part thereof. The permeable portion may be permeable to water vapor but impermeable to liquid water, so that the moisture transmission pathway (TT) is provided by the permeable portion of the expiratory conduit 582. The permeable portion may include one or more materials that are water vapor breathable and allow for passage of water vapor. The permeable portion may form some or all of the walls of the expiratory gas conduit 582 (e.g., the inner tube) and may include a single, or composite layer of water vapor breathable medium. For example, in some embodiments, the permeable portion may include an inner layer and an outer layer having different permeability/wicking properties. A first wicking layer may be provided as an inner layer of inner tube and may be configured to contact the breathing gas flow (BB) inside of the inner tube. The wicking layer may be made of one or more wicking materials that allow for adsorption and/or absorption of moisture and/or water in any phase (e.g., gas and/or liquid), for example, through capillary action. The permeable portion may also include an outer layer of water vapor breathable material that permits the passage of water vapor only, while preventing passage of liquid water. It should be appreciated that the permeable portion may comprise wicking material such as those used with the moisture removal and condensation and humidity management apparatus 410 previously discussed herein.

In some embodiments, the expiratory gas conduit 582 may, additionally or alternatively, include one or more small openings or perforations (not shown) in the inner tube which permit drainage of liquid water from the breathing gas BB to the dry gas DD. Therefore, a second moisture transmission pathway may be provided by the one or more perforations between the breathing gas flow (BB) and dry gas flow (BD). It should be appreciated that the transmission pathways may be provided in the alternative and/or at different portions along the breathing circuit tubing. Moreover, the transmission pathway (TT) and the second transmission pathway may be provided in a gradient along the length of the expiratory gas conduit 582. For example, in some embodiments, the inner tube may have more permeability at an upstream end than a downstream end, thus resulting in increased moisture transfer when the breathing gas enters the breathing gas conduit, and further resulting in reduced condensation in the remaining length of the inner tube. In some embodiments, the inner tube may have more permeability on the downstream end than the upstream end, thus increasing moisture transfer when the moisture of the breathing gas is lower.

According to another aspect of the present disclosure, a method or process for on-demand near-patient humidification provides simultaneous, independent control of the temperature and humidity of the inspiratory gas flow. Control of inspiratory airflow heat and humidity is achieved by the addition of precise control of mass flow and temperature of steam into a cold, dry airflow. The method or process may comprise a humidity control algorithm. Such an humidity control algorithm considers patient breathing as either expiration or inspiration. The humidity control algorithm also considers each breath in relative time with the starting breath inhalation t=0. The humidity controls must first determine the patient breathing rhythm. While the rhythm is indeterminate, the controls will heat and inject water as a function of current air flow and temperature. Following detection of the first complete patient breath, the humidity controls continue to heat and inject water as a function of current air flow/temp. These water values are collected into a mathematical array and assigned a relative time in the breath into a second array. Once the patient's exhalation is complete, the system waits for the next inhalation-to-exhalation transition. During the next patient breath, the humidity control rotates the calculated water array to the end of the array. This data is shifted forward in time by the breath cycle time period. The formula for the time shifted data may be represented as: $W_n(t)=W_{n-1}(t+t_{period})$, wherein $W_n$ is the previous patient breath.

For subsequent patient breaths, the system heats and injects the volume of water corresponding to the time-shifted data calculated from the previous patient breath, $W_n(t)$. The controls continue to calculate water output as a function of current air flow and stores this information for use in the next patient breath. The controls also continue to wait for the next inhalation-to-exhalation transition, using interpolation when actual breath flow measurements do not correspond to predicted values, within a defined tolerance zone. Therefore, if the patient breathes spontaneously, humidity controls immediately detect this condition to revert immediately to heating and injecting water as a function of air flow rate. The humidity controls are effectively reset to initial start-up conditions.

At initial start-up, temperature control temporarily overrides humidity control in priority. A default water flow rate as a function of air flow rate is used during initial start-up. Humidity control begins once temperature stability is achieved. The humidity control analyzes absolute humidity measurements, calculations, or estimates of previous patient breaths and uses this data to adjust the control algorithm. Because steam possesses significant amounts of energy, a small change in water flow results in a large change in temperature. Therefore, humidity adjustments must be gradual to maintain temperature stability. Therefore, a running average proves a good control variable for humidity control algorithms. Longer running averages generally provide greater stability but reduce response time. Shorter running averages sacrifice stability for increased response time.

The system for on-demand near-patient humidification of the present disclosure permits precise humidity control by controlling the amount of moisture in the form of vapor or steam that is mixed within the respiratory airflow. Absolute humidity is determined as the ratio of mass flow of moisture divided by the volume of dry air. The system may further measure the volumetric (or mass) flow rate of air, and injects the appropriate amount of water based on this measurement. The system may also permit precise humidity control by controlling the timing when moisture is introduced into the air flow, thus preventing humidification of the airstream during non-inhalation. Whereas conventional humidification devices humidify air continuously, which causes PEEP bias flow to be humidified, such excess humidity is wasted and introduces additional moisture into the exhalation circuit which often generates condensation. By timing the humidification of the air flow with patient inhalation, the present system is able to reduce water consumption and subsequent condensation. Moreover, air flow measurements for humidity control may be acquired from data provided by a companion respiratory ventilator or a separate measurement instrument.

Figure 23:
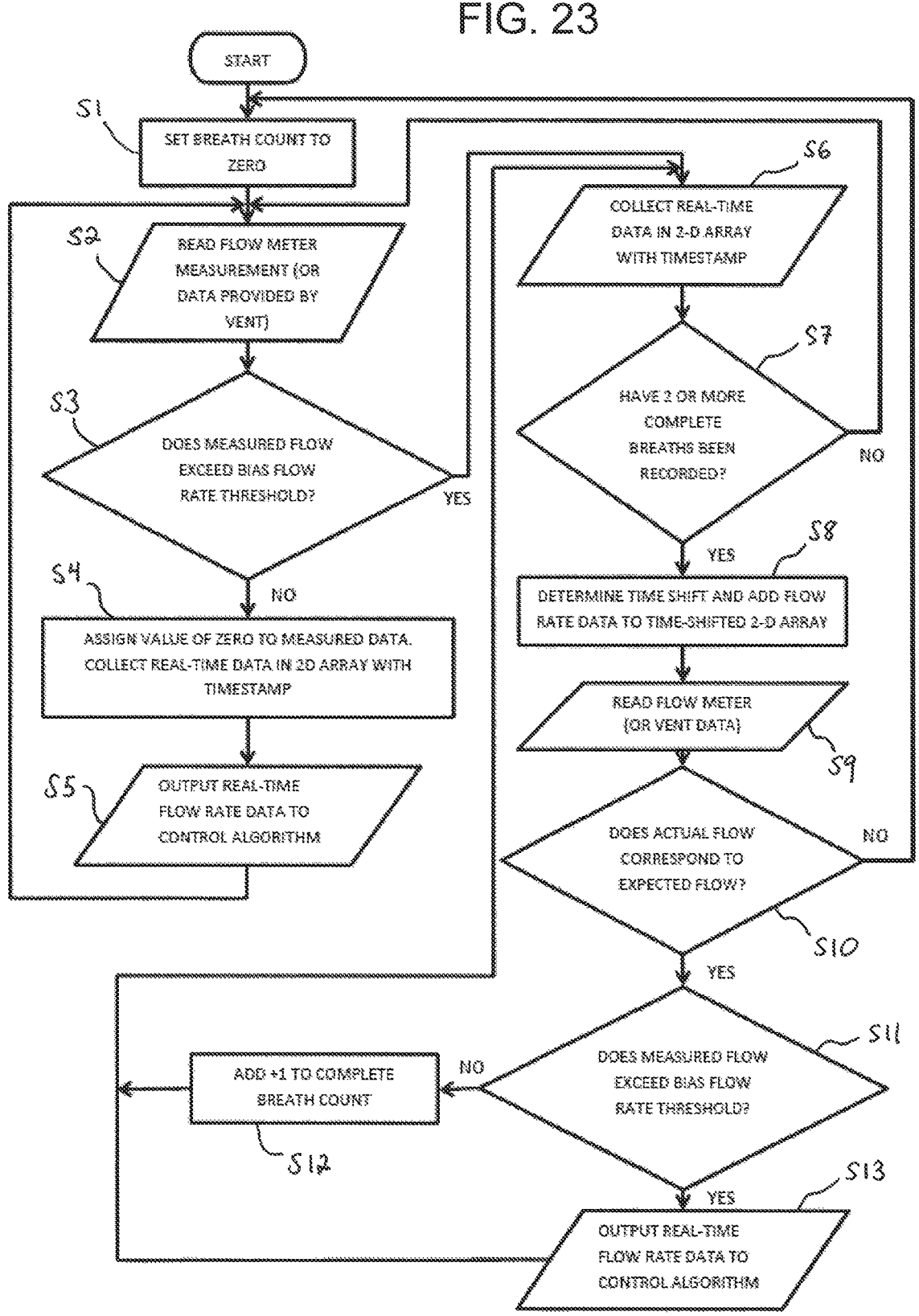
FIG. 23 is a flowchart depicting a algorithm for determining patient breathing cycle according to an aspect of the disclosure.

Turning to FIG. 23, a flow chart illustrating the aforementioned process for analyzing the timing of previous patient breaths in order to predict the next patient breath is shown. This process permits the addition of heat and moisture in advance of a breath in order to simultaneously improve mixing of humidity into the air flow and improve temperature control. In a first step S1, the patient breath count is set to zero. In step S2, the flow meter measurement is read, or data is provided by the vent. If the measured flow does not exceed the bias flow rate threshold in S3, a value of zero is assigned to the measured data. Real-time data is further collected in a two-dimensional array with a corresponding timestamp in step S4. In step S5, real-time flow rate data is then output to the control algorithm, and step S2 is then repeated.

Referring again to step S3, if the measured flow does exceed a bias flow rate threshold, then real-time data is collected in a two-dimensional array with a corresponding timestamp in step S6. In step S7, a determination is made as to whether two or more complete breaths have been recorded. If two or more complete breaths have not been recorded, then step S2 is repeated. If two or more complete breaths have been recorded, then a time shift is determined in step S8 and the flow rate data is added to the time-shifted two-dimensional array. Thereafter, the flow meter (or vent data) is read in step S9. In step S10, if the actual flow does not correspond to the expected flow, then step S1 is repeated. Alternatively, if the actual flow does correspond to the expected flow, then step S11 is performed which determines whether the measured flow exceeds a bias flow rate threshold. If the measured flow does not exceed a bias flow rate threshold, then a breath is added to the complete breath count, and step S6 is repeated. Alternatively, if the measured flow does exceed the bias flow rate threshold in step S11, then the real-time flow rate data is output to the control algorithm in S13.

Measurement of humidity of incoming air can be used to reduce the amount of moisture added to the air flow, thereby improving humidity control. The mathematical formula for rate of water addition to the airstream assumes incoming air with zero humidity. The flow rate is adjusted to compensate for incoming humidity within incoming air and/or moisture introduced through permeable membrane in the expiratory limb of the circuit. The system is configured to control absolute humidity (mass of water vapor divided by the volume of incoming dry air). However, control of relative humidity (RH) is possible if pressure transducer(s) are incorporated into the system to solve the equations required for calculating RH. Also, RH control is possible if RH measurement instruments are incorporated for control feedback. Further, it should be appreciated that additional control may be gained by determining the rate moisture is transferred through the permeable membrane, and including this rate into the controls algorithm for improved humidity control.

While the system and method for on-demand near-patient humidification has been described in terms of what may be considered to be specific aspects, the disclosure need not be limited to the disclosed aspects. As such, this disclosure is intended to cover various modifications and similar arrangements that fall within the spirit and scope of the claims, which should be accorded their broadest interpretation so as to encompass all such modifications and similar structures. The present disclosure is considered as illustrative and not restrictive.

The invention claimed is:

1. A near-patient humidification system for providing vapor to a respiratory breathing circuit, the system comprising:
   an expiratory gas conduit configured to transport an expiratory gas flow from a patient;
   an inspiratory gas conduit configured to transport an inspiratory gas flow to the patient;
   a patient coupling member configured to couple the expiratory and inspiratory gas conduits to a patient interface, the patient coupling member having a housing defining an expiratory gas passage in communication with the expiratory gas conduit, an inspiratory gas passage in communication with the inspiratory gas conduit, a proximal end having an expiratory gas outlet and at least one inspiratory gas inlet, and a distal end having an expiratory gas inlet and an inspiratory gas outlet; and
   a vapor injection unit located at least partially within the housing of the patient coupling member, the vapor injection unit having a vapor housing and a heater assembly, a portion of the vapor injection unit passing through the expiratory gas passage and the expiratory gas being permitted to flow around the portion of the vapor injection unit, the heater assembly configured to heat a supply of fluid into vapor and to inject the vapor into the inspiratory gas passage of the patient coupling member at a vapor injection location for providing humidity to the inspiratory gas flow, the heater assembly comprising a heating element and a heater element, the heating element provided within the vapor housing and configured to vaporize the supply of fluid, and the heater element configured to heat the heating element.

2. The near-patient humidification system according to claim 1, wherein the vapor housing includes a proximal end and a distal end, and the vapor housing defining a housing lumen extending from the proximal end to the distal end.

3. The near-patient humidification system according to claim 1, wherein the vapor injection unit further comprises a cannula defining an inner lumen configured to receive a flow of water, and wherein the inner lumen is in fluid communication with the inspiratory gas passage of the patient coupling member.

4. The near-patient humidification system according to claim 3, wherein the heater assembly is an induction heater assembly, and wherein the vapor injection unit further comprises an induction element surrounding at least a portion of the cannula.

5. The near-patient humidification system according to claim 4, wherein the induction element comprises at least one helically wound metallic coil.

6. The near-patient humidification system according to claim 4, wherein the induction element comprises one or more electrical conductors configured to generate an oscillating magnetic dipole.

7. The near-patient humidification system according to claim 4, wherein the induction element comprises at least two electrical conductors configured to generate an oscillating magnetic multipole.

8. The near-patient humidification system according to claim 7, wherein the at least two electrical conductors are wires or a printed circuit.

9. The near-patient humidification system according to claim 4, the heating element being located inside the cannula and at least partially surrounded by the induction element; wherein the induction element is configured to be excited by electrical current supplied from a power assembly, to generate an oscillating magnetic field to create eddy currents in the heating element to heat the heating element, and thereby heat the flow of water in the cannula flowing past the heating element, to thereby vaporize the water into steam which exits the vapor injection unit to be injected into the inspiratory gas passage.

10. The near-patient humidification system according to claim 9, wherein the heating element comprises Mu-metal.

11. The near-patient humidification system according to claim 9, wherein the heating element includes a magnetic material with a relative magnetic permeability greater than one.

12. The near-patient humidification system according to claim 9, wherein the heating element comprises a rolled foil spirally disposing a plurality of layers of said foil.

13. The near-patient humidification system according to claim 9, wherein the heating element comprises a wire mandrel and a foil wrapped around the wire mandrel in a spiral pattern disposing a plurality of layers of said foil.

14. The near-patient humidification system according to claim 1, wherein the patient coupling member housing includes the proximal end configured to releasably engage the expiratory and inspiratory gas conduits, and the distal end configured to releasably engage a patient interface.

15. The near-patient humidification system according to claim 1, further comprising a vent coupling member adapted to releasably couple the expiratory and inspiratory gas conduits to a ventilator.

16. The near-patient humidification system according to claim 1, wherein the expiratory and inspiratory gas conduits are concentrically arranged, such that the expiratory gas conduit defines an inner conduit and the inspiratory gas conduit defines an outer conduit.

17. The near-patient humidification system according to claim 16, wherein the expiratory gas conduit is configured to permit moisture to permeate through walls of the expiratory gas conduit so that humidity or water vapor in the expiratory gas flow can be transferred to the inspiratory gas flow in the inspiratory gas conduit.

18. The near-patient humidification system according to claim 1, further comprising a first sensor configured to measure a temperature and a humidity of the inspiratory gas flow independently at a location upstream from the vapor injection location, and a second sensor configured to measure a temperature and a humidity of the of the inspiratory gas flow independently at a location downstream from the vapor injection location.

19. The near-patient humidification system according to claim 1, wherein the vapor housing having a proximal end and a distal end, the vapor housing defining a housing lumen extending from the proximal end to the distal end, and wherein the vapor injection unit includes a hub connected to the proximal end of the vapor housing and being configured to connect to a fluid supply.

20. The near-patient humidification system according to claim 1, further comprising a check valve proximal to the heating element.

21. The near-patient humidification system according to claim 1, wherein the vapor housing having a proximal end and a distal end, the vapor housing defining a housing lumen extending from the proximal end to the distal end, and wherein the vapor housing comprises a thermally insulating material.

22. The near-patient humidification system according to claim 1, wherein the vapor housing having a proximal end and a distal end, the vapor housing defining a housing lumen extending from the proximal end to the distal end; wherein the vapor injection unit further comprises a cannula defining an inner lumen configured to receive a flow of water; wherein the inner lumen is in fluid communication with the inspiratory gas passage of the patient coupling member; and wherein the cannula is made from a material selected from metal, plastic, glass, ceramic, and a combination thereof.

23. The near-patient humidification system according to claim 1, wherein the vapor injection unit further comprises a power assembly for connection to an electrical power source.

24. The near-patient humidification system according to claim 23, wherein the power assembly is located at a proximal end of the vapor housing.

25. A method of simultaneously and independently controlling the temperature and humidity of inspiratory gas in a respiratory breathing circuit, the method comprising:
  providing the near-patient humidification system as claimed in claim 1;
  supplying a breathing gas to the respiratory breathing circuit;
  measuring a first temperature and a first humidity of the breathing gas at a location upstream from the vapor injection unit;
  measuring a second temperature and a second humidity of the breathing gas at a location downstream from the vapor injection unit; and
  injecting vapor from the vapor injection unit into the respiratory breathing circuit, the vapor having a vapor temperature determined as a function of the measured first and second temperatures and the measured first and second humidities of the breathing gas.

* * * * *